(12) United States Patent
Kwon et al.

(10) Patent No.: US 7,749,732 B2
(45) Date of Patent: Jul. 6, 2010

(54) METHOD FOR PREPARING ACTIVE NANOARCHAEUM EQUITANS DNA POLYMERASE AND THE ACTIVE DNA POLYMERASE PREPARED BY THE METHOD

(75) Inventors: Suk-Tae Kwon, Gyeonggi-do (KR); Jeong Jin Choi, Seoul (KR); Ki Hoon Nam, Daegu (KR)

(73) Assignee: Sungkyunkwan University Foundation for Corporate Collaboration, Gyeonggdo (KR)

( * ) Notice: Subject to any disclaimer, the term of this patent is extended or adjusted under 35 U.S.C. 154(b) by 672 days.

(21) Appl. No.: 11/580,485

(22) Filed: Oct. 13, 2006

(65) Prior Publication Data

US 2007/0154913 A1    Jul. 5, 2007

(30) Foreign Application Priority Data

Nov. 15, 2005   (KR) ..................... 10-2005-0109371

(51) Int. Cl.
*C12P 21/02* (2006.01)
*C12N 15/00* (2006.01)

(52) U.S. Cl. .................................. 435/69.1; 435/320.1

(58) Field of Classification Search ........................ None
See application file for complete search history.

(56) References Cited

OTHER PUBLICATIONS

Choi et al., J. Mol. Biol. (2006) 356, 1093-1106 (available online Dec. 27, 2005).*
Huber H. et al, "A new phylum of Archaea represented by a nanosized hyperthermophilic symbiont," 2002, Nature, 417, 63-67.
Waters E, et al, "The genome of Nanoarchaeum equitans: Insights into early archaeal evolution and derived parasitism ," 2003, Proc. Natl Acad. Sci USA 100, 12984-12988.
Perler, F. B. et al, "Protein splicing elements: inteins and exteins—a definition of terms and recommended nomenclature," 1994, Nucleic Acids Res 22, 1125-1127.
Kane, P. M. et al, "Protein Splicing Converts the Yeast TFP1 Gene Product to the 69-kD subunit of the Vacuolar H+-Adehosine Triphoshatase," 1990, Science 250, 651-657.
Martin, D.D. et al, "Characterization of a Naturally occurring Trans-Splicing Intein from *Synechocystis*," 2001, Biochemistry 40, 1393-1402.
Caspi J., et al, "Distribution of Split DnaE inteins in cyanobacteria," 2003, Mol Microbiol 50, 1569-1577.
Wu, H et al, "Protein trans-splicing by a split intein encoded in a split DnaE gene of *Synechocystis* sp. PCC6803," 1998, Proc Natl Acad Sci USA 95, 9226-9231.
Evans, T.C. Jr., et al, "Protein trans-Splicing and Cyclization by a Naturally Split Intein from the dnaE Gene of *Synechocystis* Species PCC6803," 2000, J Biol Chem 275, 9091-9094.
Kelman, Z. et al, "Isolation and Characterization of a Split B-type DNA Polymerase from the Archaeon Methanobacterium thermoautotrophicum H," 1999, J. Biol Chem. 274, 28751-28761.
Braithwaite, D.K. et al, "Compilation, alignment and phylogenetic relationship of DNA polymerases," J. 1993, Nucleic Acids Res. 21, 787-802.
Blanco, L. et al, "A general Structure for DNA-dependent DNA polymerases," 1991, Gene 100, 27-38.
Truniger, V. et al, "A SNA binding motif coordinating synthesis and degradation in proofreading DNA polymerases," 1996, EMBO J. 15, 3430-3441.
Smith, D.R. et al, "Complete genome sequence of Methanobacterium thermoautotrophicum deltaH: functional analysis and comparative genomics ," 1997, J. Bacteriol 179, 7135-7155.
Uemori, T. et al, "Organization and nucleotide sequence of the DNA polymerase gene from the archaeon *Pyrococcus furiosus*," 1993, Nucleic Acids Res, 21, 259-235.
Pietrokovski, S. "Modular organization of inteins and C-terminal autocatalytic domains," 1998, Protein Sci., 7, 64-71.

* cited by examiner

*Primary Examiner*—Nancy Vogel
(74) *Attorney, Agent, or Firm*—Casimir Jones, S.C.

(57) ABSTRACT

Disclosed are a method of preparing an active *Nanoarchaeum equitans* B-type DNA polymerase (Neq DNA polymerase), an active Neq DNA polymerase prepared according to the method, and a polymerase chain reaction (PCR) using the active Neq DNA polymerase. The active Neq DNA polymerase may be used in various nucleic acid polymerization reactions, such as PCR.

7 Claims, 7 Drawing Sheets

Fig.1
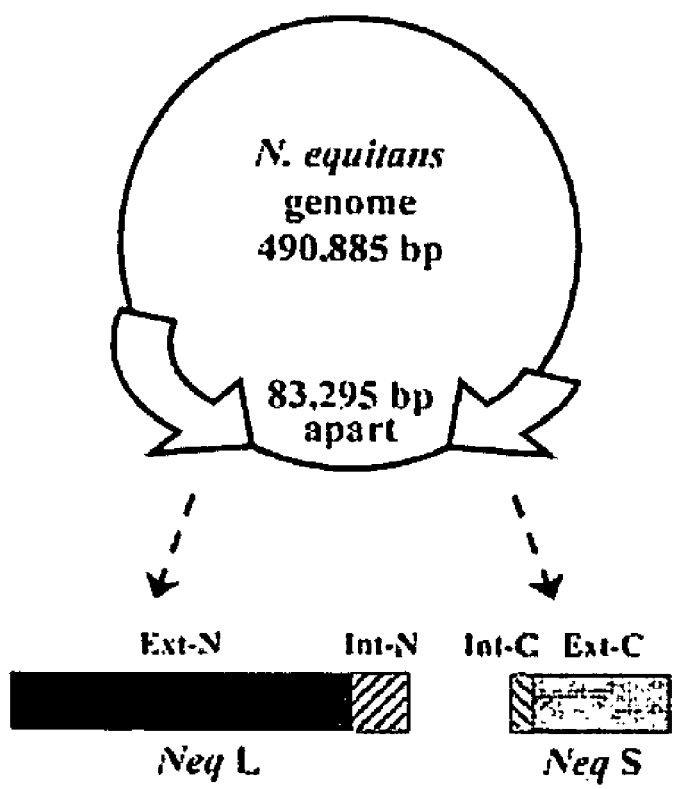
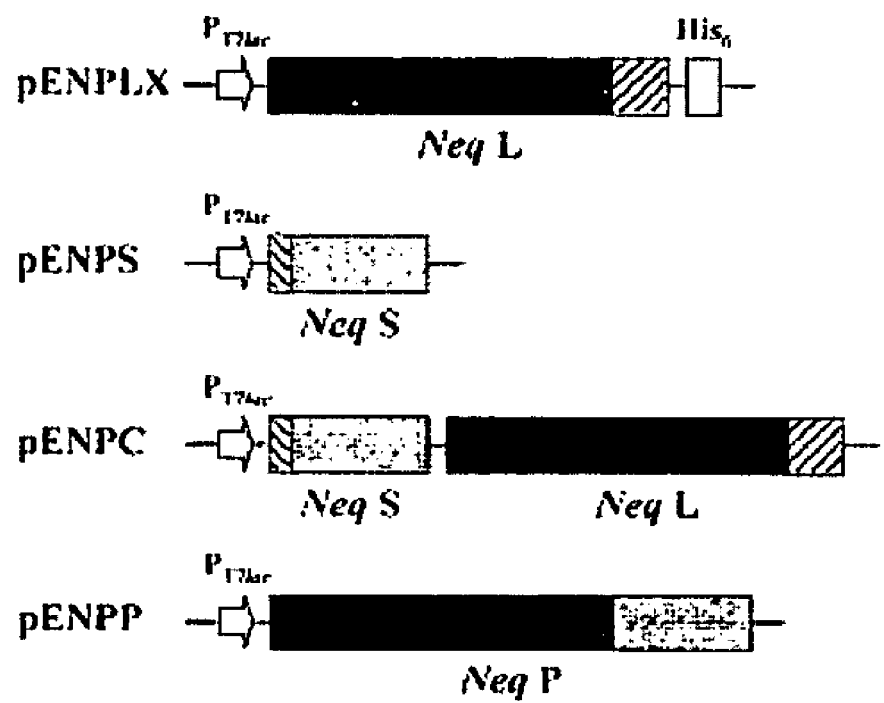

Fig. 2

A. DNA polymerase sequence alignment

```
Neq   1   MLHQLPTMVVEEKAVKEEEGYSVLKCYWINIENTPLDEVILTGKDENNRACEVIIPYKWYFYFEGDIKDLEEFANNKKIK
Mth   1       MEDYRMVLLDIDYVTVDEVPVIRLFG    KDKSGGNEPIIAHDRSFRPYIYAIPTDLDECLRELEELELEK
Pfu   1          MILDVDYITEEGKPVIRLFK    KENGKFK   IEHQRTFRPYIYALLRD DSKIEEVKKITGERHGKIVRI

Neq  81   IEYTKEQKKYIEKPKDVYKVYVLH KHYPILKEFIKEKGYKK  YETDINVYRKFLIDKGIEPFEWFEVEGKILLSTSN
Mth  69        LEVKEMRDLGRPTEVIRIEFRHPQDVPKIRDRIRDLESVRDIREHDIPFYRRYLIDKSIVPMEELEFQGVEVDSAPSV
Pfu  66        VDVEKVEKKFLGKPITVWKLYLEHPQDVPTIREKVREHPAVVDIFEYDIPFAKRYLIDKGLIPME
                                                                Exo I
Neq 157              KVRIKAQSIKRLYEKTKPSVLAFDIEV YSEAFPNPEKDKIISTALYGD NYEGVISYKGEP  TIKVNTEYEL
Mth 147        TTDVRTVEVTGRVQSTGSGAHGLDILSEDIEVRNPHGMPDPEKDEIVMIGVAGNMGYESVISTAGDHLDFVEVVEDEREL
Pfu 131                  GEEELKILAFDIETLYHEG EEFGKGPIIMISYADE NEAKVITWKNIDLPYVEVVSSEREM
                              Exo II
                 Pol IV
Neq 227   IEKFVEIIESLKPDIIVTYNGDNFDIDFLVKRASLYNIRLPIKLVNKKEPIYNFRESAHVDLYKTIITT      IYKTQLST
Mth 227   LERFAEIVIDKKPDILVGYNSDNFDFPYITRRAAILGAELDLGWDGSKIRTMRRGFANATAIKGTVHVDLYPVMRRYMNL
Pfu 191   IKRFLRIIREKDPDIIVTYNGDSFDFPYLAKRAEKLGIKLITIGRDGSEPKMQRIGDMTAVEVKGRIHFDLYHVITRTINL
                                                           Exo III
Neq 303   QTYSLNEVAKEILGEEKIYDYENMLYD WAIG NYNKVFEYNLKDAELITYKLFKYYENDLLELARLVNGPLFDVSRFSYS
Mth 307   DRYTLERVYQELFGEEKIDLPGDRLWEYWDRDELCRDELFRYSLDDVVATHRIAEKILPLNLELTRLVGQPLFDISRMATG
Pfu 271   PIYTLEAVYEAIFGKPKEKVYADEIAKAWESGENLERVAKYSMEDAKATYELGKEFLPMEIQLSRLVGQPLWDVSRSSTG
                                           DNA binding motif
                                                                          Pol II
Neq 381   NIVEWYLIKKSRKYNEIVPNKPKMEEVERRKLNTYAGAFVYEPKPGLYENLAVLDFASLYPSIILEHNVSPGTIYCEHDD
Mth 387   QQAEWFLVRKAYQYGELVPNKPSQSDFSSRRGRRAVGGYVKEPEKGLHENIVQFDFRSLYPSIIISKNISPDTL   TDDE
Pfu 351   NLVEWFLLRKAYERNEVAPNKPSEEEYQRRLRESYTGGFVKEPEKGLWENIVYLDFRALYPSIIITHNVSPDTL   NLEG
                  Pol VI                                                   Pol III
Neq 461   CKQNGVEAIINNEKKYVWFCKKVKGFIPTVLEHLYTKRLELKRKLKELDRDSEEYKIINAKQAVLKIIINATYGYMGFPN
Mth 465   ESECYVAPEYGYR      FRKSPRGFVPSVIGEILSERVRIKEEMKGSD DPMERKILNVQQEALKRLANTMYGVYGYSR
Pfu 429   CKNYDIAPQVGHK      FCKDIPGFIPSLLGHLLEEROKIKTKMKETQ DPIEKILLDYRQKAITKLLANSFYGYYGYAK
                                                                   Pol I
Neq 541   ARWYCIDCAAAVAAWGRKYINYILKRAEEE GFKVIYGD[Int-N](split)[Int-C]TDSLFISGD
Mth 539   FRWYSMECAEAITAWGRDYIKKTIKTAEE FGFHTVYAD────────────────TDGFYATYRG(split)MSQ
Pfu 503   ARWYCKECAESVTAWGRKYIELVWKELEEKFGFKVLYID────────────────TDGLYATIPG────GES
                                                                        Pol V
Neq 588           KDKVLEFLEKVNKELPGKIQLDLEDFYVRGIEVKKRGEQKGAKKKYALLSEQGYIKLRGFEAVRTDWAPIVK
Mth 590   LSKVEDEILSOVKRFLKHINSNLPEGMELEFEGFYRRGFFV   TKKRYALIEDD_TIVAKGLELVRRDWAPIAK
Pfu 555   EEIKKKALEFVKYINSKLPGLLELEYEGFYKRGFFV       TKKRYAVIDEEGKVITRGLEIVRRDWSEIAK Neq 660   EVQTKLLEILLKEGNIEKAROYIKEIIRKLRNREIPWEKLLITETIRKPLEKYKVEAPHVAAAKKYKRLGYKVMPGFRVR
Mth 661   KTORKVLMAILRDGSPEKAREILREVVGRIRRGDVELDDLVIHTQIITRDLSEYKQIGPHVIAAKRSLEKGRRVERGSIVR
Pfu 622   ETQARVLETIILKHGDVEEAVRIVKEVIOKLANYEIPPEKLAIYEQITRPLHEYKAIGPHVAVAKKLAAKGVKIKPGMVIG Neq 740   YLVVGSTGRVSDRIKIDK    EVRGNEYDPEYYIEKQLLPAVEQILESVGIKDTFTGKKLTDFFK
Mth 741   YIIVKGRGPISQRAFPVE   DAEGMGYDPDYYIENQVMAAVSRIMSSLGYSTEDMNSLSSGERQSSLDAFF
Pfu 702   YIVLRGDGPISNRAILAEEYDPKKHKYDAEYYIENQVLPAVLRILEGFGYRKEDLRYQKT ROVGLTSWLNIKKS
```

B. Split mini-intein sequence alignment

```
              Block A                                                            Block B
Neq   SIM DTEIEVIENGIKKKEKLSDLFNKYYAGFQIGEKHYAFPPDLYVYD GERWVKVYSIIKHETETDLYEINGITLSANHLVLS
Ssp   CLSFGTEILTVEYGPLPIGKIVSEEINCSVYSVDPEGRVYTQAIAQWHDRGEQEVLEY.           ELEDGSVIRATSDHRFLT
                                                  Int-N ←     → Int-C          Block F
Neq   KGNWVKAKEYENKNN                            (split)      WRYEGKKRVILYDLSTESG KFYV
Ssp   TDYQLLAIEEIFARQLDLLTLENIKQTEEALDNHRLPFPLLDAGTIK(split)MVKVIGRRSLGVQR I FDIGLPQDHNFLLA
              Block G ─→Ext-C
Neq   NGLVLHNT
Ssp   NGAIAANC
```

Fig. 7
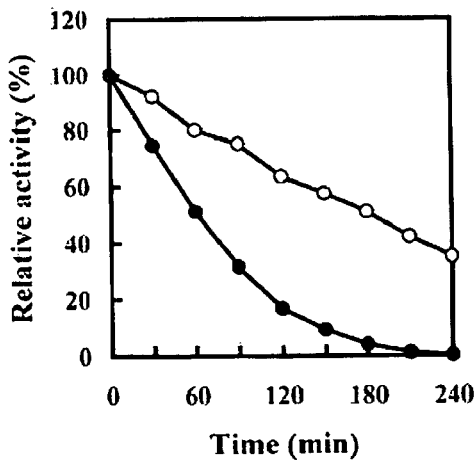
Fig. 8
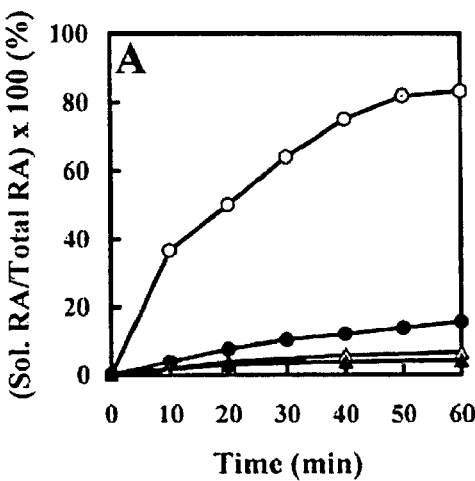
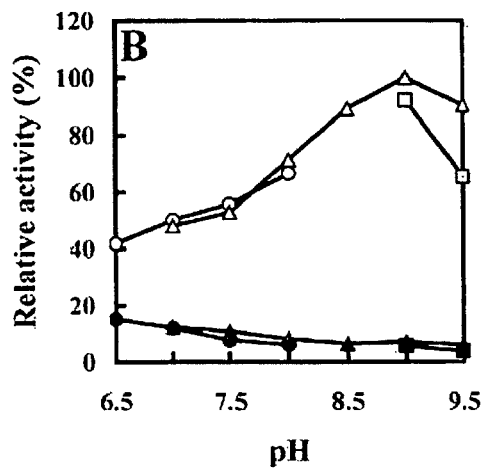
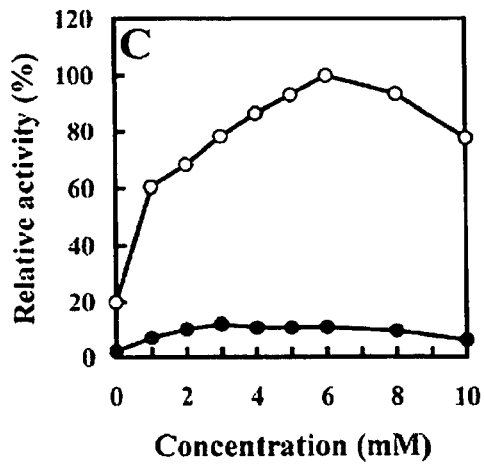
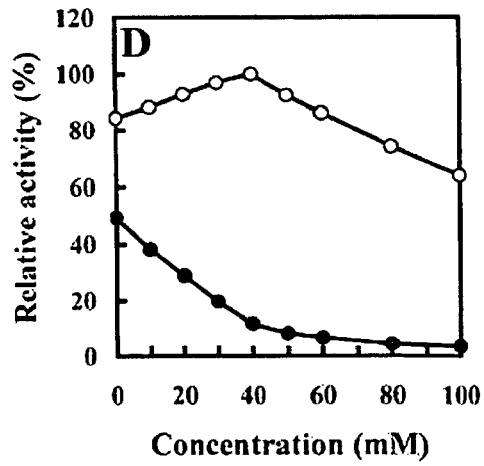

US 7,749,732 B2

METHOD FOR PREPARING ACTIVE NANOARCHAEUM EQUITANS DNA POLYMERASE AND THE ACTIVE DNA POLYMERASE PREPARED BY THE METHOD

TECHNICAL FIELD

The present invention relates to a method of preparing an active *Nanoarchaeum equitans* B-type DNA polymerase (hereinafter, referred to as "Neq DNA polymerase"), an active Neq DNA polymerase prepared according to the method, and a polymerase chain reaction (hereinafter, referred to as "PCR") using the active Neq DNA polymerase.

BACKGROUND ART

Recently, a novel archaeal phylum, the Nanoarchaeota, was identified. The representative species *Nanoarchaeum equitans* is an extremely tiny (nano-sized), hyperthermophilic anaerobe which was isolated from a submarine hot vent at the Kolbeinsey ridge, north of Iceland (see, Huber, H. et al., 2002, *Nature* 417, 63-67). This organism grows on the surface of a specific crenarchaeal host, *Ignicoccus* sp. strain KIN4/I, under strictly anaerobic conditions between 70 and 98° C. The genome (490,885 base pairs (hereinafter, referred to as "bp")) of *N. equitans*, one of the smallest microbial genomes, has been completely sequenced (see, Waters, E. et al., 2003, *Proc. Natl. Acad. Sci. USA* 100, 12984-12988). It was deduced from the genome sequence analysis that *N. equitans* is a parasite for *Ignicoccus* sp. strain KIN4/I.

Deoxyribonucleic acid polymerases (DNA polymerases; E.C. number 2.7.7.7) are enzymes that synthesize DNA in the 5' to 3' direction on template DNA. These enzymes play leading roles in cellular DNA replication and repair (see, Lehninger, A. L. et al., 1993, *Principles of Biochemistry*, 2nd ed., Worth Publishers). Beginning with the discovery and characterization of DNA polymerase I from *Escherichia coli* by Kornberg and colleagues in 1957 (see, Kornberg, A. & Baker, T., 1992, DNA Replication, 2nd ed., Freeman Company), a variety of DNA polymerases have been isolated and identified from prokaryotic and eukaryotic sources. These DNA polymerases have been classified into five major groups based on amino acid sequence similarity: families A, B, C and D, which include DNA polymerases having high similarity to *E. coli* DNA polymerase I, II, III a subunit, and *Pyrococcus furiosus* DNA polymerase II, respectively; and family X, which includes other DNA polymerases not belonging to the A to D families (see, Braithwaite, D. K. & Ito, J., 1993, *Nucleic Acids Res.* 21, 787-802; Cann, I. K. O. & Ishino, Y., 1999, *Genetics* 152, 1249-1267).

Thermostable DNA polymerase was initially isolated and identified from a thermophile, *Thermus aquaticus* YT-1, by Chien et al. in 1976 (see, Chien, A. et al., 1976, *J. Bacteriol.* 127, 1550-1557). Thereafter, studies were made with some thermophiles, but these did not attract particular interest. However, with the development of a PCR technique using thermostable DNA polymerase by Saiki et al. in 1988 (see, Saiki, R. K. et al., 1988, *Science* 239, 487-491), thermostable DNA polymerases became of great interest, and these enzymes have been competitively developed from several thermophiles and hyperthermophiles. In particular, thermostable DNA polymerases from hyperthermophilic archaeons, such as *Thermococcus litoralis* and *P. furiosus*, have been used in PCR requiring high fidelity because they have 3'→5' exonuclease activity (this activity is known as proofreading activity) along with DNA polymerization activity (see, Mattila, P. et al., 1991, *Nucleic Acids Res.* 19, 4967-4973; Lundberg, K. S. et al., 1991, *Gene* 108, 1-6).

Inteins are protein insertion sequences that are embedded in-frame within precursor protein sequences. These sequences are removed from the precursor protein by a self-splicing process, and thus do not affect the structure and activity of the final protein made from the precursor protein (see, Perler, F. B. et al., 1994, *Nucleic Acids Res.* 22, 1125-1127). Protein splicing is a post-translational processing event in which the intein is precisely self-excised from a precursor protein with concomitant ligation of the flanking protein sequences, exteins, by a normal peptide bond (see, Kane, P. M. et al., 1990, *Science* 250, 651-657). Naturally occurring inteins, which are present in proteins of organisms, can be grouped into three types according to their structural organization: inteins, which have both self-splicing and homing endonuclease domains; mini-inteins, which lack the endonuclease domain and have the splicing domain; and split mini-inteins, lacking the endonuclease domain, in which the splicing domain exists as a split form on two separate genes, and are therefore spliced in trans (see, Martin, D. D. et al., 2001, *Biochemistry* 40, 1393-1402).

Neq DNA polymerase is encoded by two genes, which are separated by 83,295 bp on the chromosome and individually contain a deduced split mini-intein sequence (see, Waters, E. et al., 2003, *Proc. Natl. Acad. Sci. USA* 100, 12984-12988). The sequences of naturally occurring split mini-inteins, among about 180 known inteins, have been found only in several cyanobacterial C-type DNA polymerase III α subunits (hereinafter, referred to as "DnaE proteins") (see, Caspi, J. et al., 2003, *Mol. Microbiol.* 50, 1569-1577). Among them, various studies have been made only on *Synechocystis* sp. PCC6803 DnaE protein (hereinafter, referred to as "Ssp DnaE protein")(see, Wu, H. et al., 1998, *Proc. Natl. Acad. Sci. USA* 95, 9226-9231; Evans, T. C., Jr. et al., 2000, *J. Biol. Chem.* 275, 9091-9094; Martin, D. D. et al., 2001, *Biochemistry* 40, 1393-1402). This protein is different from Neq DNA polymerase in that it is derived not from archaea but from bacteria, is not a thermostable protein but a mesophilic or psychrophilic protein, and is not a B-type DNA polymerase but a C-type DNA polymerase. In addition, Methanothermobacter thermautotrophicus B-type DNA polymerase is encoded by two separated genes, but polypeptides made therefrom lack an intein and are thus active as a dimmer (see, Kelman, Z. et al., 1999, *J. Biol. Chem.* 274, 28751-28761).

PCR is a technique for exponentially amplifying a trace amount of template DNA using a DNA polymerase and primers. PCR amplification occurs in repeated cycles of three steps: DNA denaturation at 94° C., primer annealing at 40-65° C. and DNA extension at 72° C. Since the reaction requires high temperature, it is indispensably necessary to develop thermostable DNA polymerases, which are the most important factor in PCR, for the development and application of various PCR techniques (see, Erlich, H. A., 1989, *PCR Technology: Principles and Applications for DNA Amplification*, Stockton Press). Thermostable DNA polymerases are enzymes that are very useful in the identification and amplification of genes, DNA sequencing and clinical diagnosis by PCR. These enzymes are used in a wide spectrum of fields ranging from genetic engineering and molecular biology experiments to the diagnosis of hereditary diseases, early diagnosis of oncogenes and viral genes, and forensic medicine, and are thus increasing in demand.

To date, there has been no report involving the expression of any protein-encoding gene and the purification, biochemical properties and industrial application of any protein from the hyperthermophilic nanoarchaeon *N. equitans*. Also, there has been no report stating that an archaeal protein, a thermostable protein and a B-type DNA polymerase possess a split mini-intein.

Based on this background, the present inventors performed the sequence analyses of two genes encoding B-type DNA polymerase from *N. equitans*, and established methods of preparing active Neq DNA polymerase using a genetic engineering technique. The present inventors found that the active Neq DNA polymerase prepared according to the methods is applicable to general PCR and to PCR in the presence of deoxyuridine 5'-triphosphate (hereinafter, referred to as "dUTP"), thereby leading to the present invention.

DISCLOSURE OF THE INVENTION

It is therefore an object of the present invention to provide a recombinant vector which comprises the gene coding for the large fragment of Neq DNA polymerase and the gene coding for the small fragment of Neq DNA polymerase, and expresses the large and small fragments of Neq DNA polymerase.

It is another object of the present invention to provide a recombinant vector which comprises the extein-encoding region of the gene for the Neq DNA polymerase large fragment and the extein-encoding region of the gene for the Neq DNA polymerase small fragment, wherein the extein-encoding region of the gene for the Neq DNA polymerase large fragment is located upstream and the extein-encoding region of the gene for the Neq DNA polymerase small fragment is located downstream in a 5' to 3' direction, and expresses an active DNA polymerase being translated into a single polypeptide.

It is a further object of the present invention to provide transformants transformed with the recombinant vectors.

It is yet another object of the present invention to provide methods of preparing an active Neq DNA polymerase using the recombinant vectors.

It is still another object of the present invention to provide an active Neq DNA polymerase prepared using the methods.

It is still another object of the present invention to provide a method of performing a nucleic acid amplification reaction using the active Neq DNA polymerase.

BRIEF DESCRIPTION OF THE DRAWINGS

The above and other objects, features and other advantages of the present invention will be more clearly understood from the following detailed description taken in conjunction with the accompanying drawings, in which:

FIG. 1 shows a schematic gene map of the Neq DNA polymerase genes on the *N. equitans* genome, structures of polypeptides made from the genes, and recombinant plasmid constructs for expressing the genes;

FIG. 2 (SEQ ID NOS:18-22) shows multiple sequence alignments in which amino acid sequences of extein and intein of Neq DNA polymerase are compared with those of other archaeal thermostable B-type DNA polymerases and intein of Ssp DnaE protein, respectively;

FIG. 7 shows the thermostability of active Neq DNA polymerase;

FIG. 8 shows the biochemical properties of Neq L and active Neq DNA polymerase with respect to 3'→5' exonuclease activity;

BEST MODE FOR CARRYING OUT THE INVENTION

Figure 3:
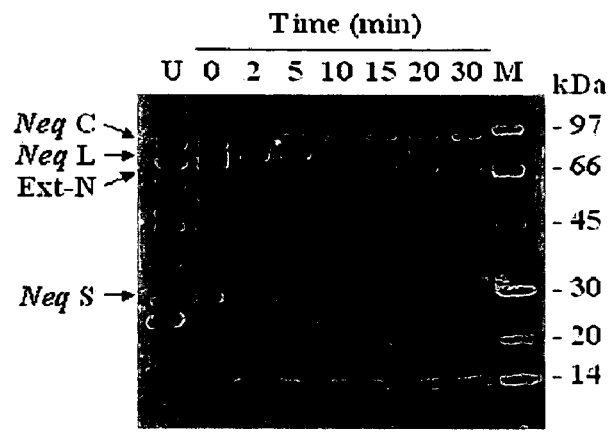
FIG. 3 shows the result of protein trans-splicing of the co-expressed Neq L and Neq S in *E. coli* BL21-CodonPlus (DE3)-RIL harboring the recombinant plasmid pENPC according to heat treatment time.

The present inventors intended to prepare active Neq DNA polymerase using the information on the complete genome sequence of *N. equitans* (see, Waters, E. et al., 2003, *Proc. Natl. Acad. Sci. USA* 100, 12984-12988). A comparison of the amino acid sequence of Neq DNA polymerase with those of already known thermostable B-type DNA polymerases revealed that Neq DNA polymerase is encoded by two genes, which are separated by over 80,000 bp on the chromosome, and that each gene consists of an extein-encoding region and a split mini-intein-encoding region. Based on the determination of the extein-encoding and intein-encoding regions in each gene, the present inventors constructed various recombinant vectors capable of producing an active Neq DNA polymerase using the two genes, each of which encodes a polypeptide not having DNA polymerization activity alone, and directly identified the expression and properties of the DNA polymerase, thereby providing methods of preparing active Neq DNA polymerase using genetic engineering techniques.

In one aspect, the present invention relates to a DNA polymerase derived from *N. equitans*.

The term "DNA polymerase", as used herein, refers to an enzyme that has a catalytic activity of forming a new single DNA strand using a single DNA strand as a template, that is, is able to polymerize deoxyribonucleoside 5'-triphosphate (hereinafter, referred to as "dNTP"), complementary to a template, to the 3' —OH of a primer. The DNA polymerase of the present invention is a thermostable B-type DNA polymerase derived from the hyperthermophilic nanoarchaeon *N. equitans*. Neq DNA polymerase is produced by genes coding for the large fragment of Neq DNA polymerase and the small fragment of Neq DNA polymerase. Neq DNA polymerase is initially expressed as two polypeptides from two genes, which are separate on the chromosome. The two polypeptides are then linked by a peptide bond to form a single protein through protein trans-splicing, thereby yielding an active DNA polymerase. The term "active Neq DNA polymerase", as used herein, means the state in which the extein of the Neq DNA polymerase large fragment is linked with the extein of the Neq DNA polymerase small fragment by a peptide bond to form a single chain.

In this specification, the large fragment of Neq DNA polymerase consists of an extein region of 578 amino acid residues, which corresponds to the amino-terminal part (N-terminal part) of Neq DNA polymerase, and an intein region of 98 amino acid residues, which corresponds to the N-terminal part of a split mini-intein participating in protein trans-splicing. Herein, the Neq DNA polymerase large fragment is designated "Neq L". Also, in this specification, the small fragment of Neq DNA polymerase consists of an intein region of 30 amino acid residues, which corresponds to the carboxyl-terminal part (C-terminal part) of the split mini-intein, and an extein region of 223 amino acid residues, which corresponds to the C-terminal part of Neq DNA polymerase. Herein, the Neq DNA polymerase small fragment is designated "Neq S". The present inventors found that Neq L or Neq S alone does not have polymerase activity, and that Neq L has little proof-reading activity.

In this specification, a protein in which inteins are removed from Neq L and Neq S through protein trans-splicing and only exteins are linked by a peptide bond is designated "Neq C (protein trans-spliced form of Neq DNA polymerase)". In this specification, an extein-encoding region of the Neq DNA polymerase large fragment gene, from which an intein-encoding region is removed, is recombined with an extein-encoding region of the Neq DNA polymerase small fragment gene, from which an intein-encoding region is removed, to express as a single polypeptide chain. The resulting expressed DNA polymerase is designated "Neq P (genetically protein splicing-processed form of Neq DNA polymerase)". The present inventors found that Neq C and Neq P, prepared by different methods, are enzymes exhibiting the same activity and biochemical properties.

In another aspect, the present invention relates to (1) a recombinant vector for separately expressing the Neq DNA polymerase large fragment and the Neq DNA polymerase small fragment; and (2) a recombinant vector for expressing an active DNA polymerase, in which extein-encoding regions of the Neq DNA polymerase large fragment and Neq DNA polymerase small fragment genes, from which intein-encoding regions are removed, are recombined to be translated into a single polypeptide chain.

The term "vector", as used herein, refers to a means for expressing a protein of interest by introducing DNA into a suitable host cell. The vector includes all ordinary vectors, such as plasmid vectors, cosmid vectors, bacteriophage vectors, and viral vectors. Plasmid vectors are preferred.

A suitable expression vector includes expression regulatory elements, such as a promoter, a start codon, a stop codon, a polyadenylation signal, and an enhancer, as well as signal sequences for membrane targeting or secretion, and may be prepared in various constructions according to the intended use. A vector may also include a selectable marker that allows the selection of host cells containing the vector, and a replicable expression vector may include a replication origin. The start and stop codons must be functional in an individual to whom a genetic construct has been administered, and must be in frame with the coding sequence. Promoters may be generally constitutive or inducible. Available promoters include inducible strong promoters, such as $\lambda P_L$, lac, trp, tac, and T7 promoters. Available signal sequences include PhoA, OmpA and PelB for *E. coli* as a host; α-amylase and subtilisin for *Bacillus* species as hosts; and MFα and SUC2 for yeast host cells.

In a detailed aspect, the present invention relates to a recombinant vector which comprises the gene coding for the Neq DNA polymerase large fragment and the gene coding for the Neq DNA polymerase small fragment and expresses the large and small fragments of Neq DNA polymerase.

The vector may have diverse applications. For example, a vector in which the Neq DNA polymerase large fragment and the Neq DNA polymerase small fragment are expressed from separate promoters is available. Also available is a vector in which the large and small fragments of Neq DNA polymerase are expressed from a single promoter, and a ribosome binding site is located between the Neq DNA polymerase large fragment-encoding gene and the Neq DNA polymerase small fragment-encoding gene to express the large and small fragments of Neq DNA polymerase, not as a fusion protein but as separate polypeptides. In the detailed practice of the present invention, a recombinant vector which carries a series of the Neq S-encoding gene, a Shine-Dalgarno sequence and the Neq L-encoding gene to co-express Neq L and Neq S was constructed, and is designated "pENPC". This recombinant vector was transformed into *E. coli* BL21-CodonPlus(DE3)-RIL, thereby yielding a transformant, *E. coli* BL21-CodonPlus(DE3)-RIL/pENPC. The *E. coli* BL21-CodonPlus(DE3)-RIL harboring the recombinant vector pENPC (*Escherichia coli* BL21-CodonPlus(DE3)-RIL/pENPC) was deposited at the Korean Agricultural Culture Collection (Seodun-dong, Gwonseon-gu, Suwon Gyeonggi-do, Republic of Korea) on Sep. 21, 2005, and assigned accession number KACC95038P.

Moreover, the above *E. coli* BL21-CodonPlus(DE3)-RIL harboring the recombinant vector pENPC (*Escherichia coli* BL21-CodonPlus(DE3)-RIL/pENPC) was deposited at the Korean Culture Center of Microorganisms (Hongje-1-dong, Seodaemun-gu, Seoul 120-091, Republic of Korea) on Sep. 22, 2006, and assigned accession number KCCM10780P.

In another detailed aspect, the present invention relates to a recombinant vector which comprises the extein-encoding region of the Neq DNA polymerase large fragment gene and the extein-encoding region of the Neq DNA polymerase small fragment gene, and expresses an active DNA polymerase being translated into a single polypeptide chain.

In the vector, sequences for the extein-encoding regions of the large and small fragments of Neq DNA polymerase are linked to each other using a genetic recombination technique to translate the DNA polymerase into a single polypeptide chain in which the large and small fragments are linked by a peptide bond. Herein, in a 5' to 3' direction, the gene for the extein-encoding region of the Neq DNA polymerase large fragment is located upstream, and the gene for the extein-encoding region of the Neq DNA polymerase small fragment is located downstream. Through this vector system, an active Neq DNA polymerase may be readily prepared with no protein trans-splicing. In the detailed practice of the present invention, intein-encoding regions were removed from the two genes encoding Neq DNA polymerase, and only the remaining extein-encoding regions were sequentially linked and inserted into an expression vector. The constructed recombinant vector is designated "pENPP". This recombinant vector was transformed into *E. coli* BL21-CodonPlus(DE3)-RIL, thereby yielding a transformant, *E. coli* BL21-CodonPlus(DE3)-RIL/pENPP.

The *E. coli* BL21-CodonPlus(DE3)-RIL harboring the recombinant vector pENPP (*Escherichia coli* BL21-CodonPlus(DE3)-RIL/pENPP) was deposited at the Korean Agricultural Culture Collection (Seodun-dong, Gwonseon-gu, Suwon Gyeonggi-do, Republic of Korea) on Sep. 21, 2005, and assigned accession number KACC95039P.

Moreover, the above *E. coli* BL21-CodonPlus(DE3)-RIL harboring the recombinant vector pENPP (*Escherichia coli* BL21-CodonPlus(DE3)-RIL/pENPP) was deposited at the Korean Culture Center of Microorganisms (Hongje-1-dong, Seodaemun-gu, Seoul 120-091, Republic of Korea) on Sep. 22, 2006, and assigned accession number KCCM10781P.

In a further aspect, the present invention relates to a transformant transformed with the recombinant vector.

The transformation of the vector into host cells includes any method by which nucleic acids can be introduced into cells, and, as known in the art, may be performed by selecting suitable standard techniques according to host cells. These methods include, but are not limited to, electroporation, protoplast fusion, calcium phosphate (CaPO$_4$) precipitation, calcium chloride (CaCl$_2$) precipitation, agitation with silicon carbide fiber, agrobacterium-mediated transformation, and PEG-, dextran sulfate-and lipofectamine-mediated transformation.

Host cells suitable for transformation with the vector are preferably prokaryotic cells. Examples of prokaryotic cells include, but are not limited to, *E. coli, Rhodococcus, Pseudomonas, Streptomyces, Staphylococcus, Syfolobus, Thermoplasma, Thermoproteus, Mastigocladus, Bacillus,* and *Thermus. E. coli* is preferred. Examples of *E. coli* strains include *E. coli* XL1-blue, *E. coli* BL21(DE3), *E. coli* JM109, *E. coli* DH series, *E. coli* TOP10, and *E. coli* HB101.

In yet another aspect, the present invention relates to a method of preparing an active Neq DNA polymerase using the recombinant vector.

In detail, the present invention relates to a method of preparing an active Neq DNA polymerase, comprising (1) transforming the recombinant vector into a host cell; (2) cultivating a resulting transformant; and (3) purifying the active Neq DNA polymerase.

The method enables the establishment of a system capable of producing Neq DNA polymerase in an active form.

The host cell transformation method and the host cell type in step (1) are the same as described above.

In step (2), the cultivation of the transformant is performed by an ordinary method under suitable conditions allowing the expression of a cloned gene. This cultivation process may be readily adjusted and used according to the selected strain. The medium used for cultivation should typically contain all nutrients essential for the growth and survival of cells. The medium contains a variety of carbon sources, nitrogen sources, trace elements, and the like. The medium may also contain an antibiotic. The cultivation temperature and time of the transformant may be controlled according to cultivation conditions. Also, an inducer, such as isopropyl-β-$_D$-thiogalactopyranoside (hereinafter, referred to as "IPTG"), may be used to induce protein expression.

In step (3), the protein may be purified using an ordinary technique. For example, cells are harvested by centrifugation, disrupted using a French press, an ultrasonicator, etc., and centrifuged to eliminate cell debris, thereby obtaining the supernatant. A protein aggregated by overexpression may be dissolved and denatured in a suitable solution and then refolded (see, Kohno, 1990, *Meth. Enzym.* 185, 187-195). A solution containing the protein obtained from the host cell is subjected to ordinary protein purification processes, which may be used separately or in combination, for example, salting out (e.g., ammonium sulfate precipitation, sodium phosphate precipitation, etc.), solvent precipitation (e.g., protein fraction precipitation using acetone, ethanol, etc.), dialysis, ultrafiltration, and various chromatographies (e.g., gel filtration, ion exchange chromatography, affinity chromatography, etc.), thereby purifying the active Neq DNA polymerase protein of the present invention (see, Sambrook, J. et al., 1989, *Molecular Cloning: a Laboratory Manual*, 2nd ed., Cold Spring Harbor Laboratory Press; Deutscher, M., 1990, Guide to Protein Purification Methods, *Enzymology*, vol. 182, Academic Press).

When the active Neq DNA polymerase is prepared using the recombinant vector co-expressing the Neq DNA polymerase large fragment and the Neq DNA polymerase small fragment, step (3) further includes a process inducing protein trans-splicing of the Neq DNA polymerase large fragment and the Neq DNA polymerase small fragment. The protein trans-splicing between the fragments may be induced by incubating cell lysates at 50° C. to 100° C. Also, the heat treatment of cell lysates may be included in the method and performed with the aim of eliminating cellular proteins from hosts, such as *E. coli*, during DNA polymerase purification.

In the detailed practice of the present invention, samples heat-treated at 80° C. for 30 min are centrifuged. The supernatants are pooled, dialyzed, and then applied to an anion exchange column, UNO™ Q, and a cation exchange column, UNO™ S, in order to purify a protein of interest.

In still another aspect, the present invention relates to an active Neq DNA polymerase prepared using the method.

The active Neq DNA polymerase of the present invention, prepared according to the method, has the following properties. The active Neq DNA polymerase exhibits more than 50% DNA polymerization activity at a pH between 7.0 and 9.5. The DNA polymerase preferably has higher activity at a pH from 7.5 to 8.5, and more preferably has maximal activity at pH 8.0. The active Neq DNA polymerase has higher activity at 60 to 80° C., and more preferably has maximal activity at 70° C. The active Neq DNA polymerase exhibits more than 60% DNA polymerization activity at a magnesium ion concentration of more than 1 mM, and preferably has higher activity at 2 to 10 mM and more preferably has maximal activity at 5 mM. The active Neq DNA polymerase exhibits more than 60% DNA polymerization activity at 30 to 150 mM KCl, and preferably has higher activity at 50 to 130 mM KCl and more preferably has maximal activity at 90 to 100 mM KCl. The active Neq DNA polymerase also has 3'→5' exonuclease activity (known as proofreading activity). Moreover, the active Neq DNA polymerase has an activity of performing polymerization reaction in the presence of dUTP. That is, the present invention provides the thermostable Neq DNA polymerase, which enables polymerization reaction in the presence of dUTP and has high proofreading activity and DNA polymerization activity.

The Neq DNA polymerase provided according to the present method includes a protein having a native amino acid sequence thereof and an amino acid sequence variant of the native protein. The term "variant" of Neq DNA polymerase means a protein or a fragment thereof, which has a sequence different from a native amino acid sequence with respect to one or more amino acid residues by a deletion, an insertion, a non-conservative or conservative substitution, or a combination thereof. Amino acid exchanges in proteins and peptides which do not generally alter the activity of the proteins or peptides are known in the art (see, Neurath, H. & Hill, R. L., 1979, The Proteins, Academic Press). If desired, the protein may be modified by phosphorylation, sulfation, acrylation, glycosylation, methylation, farnesylation, and the like.

The protein variant of the present invention is a functional equivalent exerting activity identical to the native form, or preferably, a variant having a modified property. For example, the variant may exhibit enzymatic activity even at high acidity or high alkalinity at which the native protein does not show enzymatic activity, and may have enhanced structural resistance to external environments, including physical factors, such as temperature, humidity, pH, electrolytes, reducing sugars, pressure, desiccation, freezing, interfacial tension, light, repeated freezing and thawing, high concentrations, and the like; and chemical factors, such as acids, alkalis, neutral salts, organic solvents, metal ions, oxidizing and reducing agents, and the like. Otherwise, the variant may have enhanced enzymatic catalytic activity.

In still another aspect, the present invention relates to a method of performing a nucleic acid amplification reaction using the active Neq DNA polymerase.

The Neq DNA polymerase of the present invention may be used in all reactions that use a single DNA strand as a template, the reactions being based on polymerizing dNTP, complementary to the template, to the 3'—OH of a primer. A representative example is PCR. PCR is a representative nucleic acid amplification technique (NAT), which amplifies a specific DNA region of interest in vitro using a DNA polymerase, and is described in a wide range of literature (see, Mullis, K. et al., 1986, Cold Spring Harbor Symp. Quant. Biol. 51, 263-273) and U.S. Pat. Nos. 4,683,195, 4,683,202 and 4,965,188. PCR basically consists of three major steps: denaturation, in which a double-stranded template DNA is denatured into two single strands; annealing, in which primers are annealed with a target gene sequence on the single-stranded DNA; and extension, in which a DNA polymerase extends the primers and synthesizes the strand complementary to the target sequence. A specific DNA sequence is amplified while these three steps are repeated. This cycle is usually repeated 25 to 30 times. Reaction temperature may be controlled during denaturation, annealing and extension. Non-specific amplification may occur at a very low annealing temperature. Thus, taking this into consideration, the annealing temperature should be determined. Various modifications and applications are possible in the PCR method, and are included in the scope of the present invention. Examples of PCR methods include RT-PCR, Touchdown PCR, Differential Display PCR, Gradient PCR, and Real time PCR.

In particular, since the active Neq DNA polymerase provided in the present invention has polymerization activity in the presence of dUTP as described above, the combined use of the present enzyme and heat-labile uracil-DNA glycosylase may be very suitable for PCR performed for diagnosis and other purposes. Due to the PCR's property of exponentially amplifying trace amounts of DNA, any contaminating DNA in a sample containing target DNA may cause some problems even in very small amounts. Such contamination, which may occur any time during an experimental procedure, such as sample selection, nucleic acid isolation, sample transport, PCR of samples, sample recovery from gel after electrophoresis, or sample storage, is not significant in PCR for cloning purposes, but may bring about serious problems in PCR for diagnostic purposes, for example leading to false-positive results (see, Borst, A. et al., 2004, *Eur. J. Clin. Microbiol. Infect. Dis.* 23, 289-299). Some methods have been studied to solve such problems. Of them, a method developed by Longo et al. is based on carrying out a PCR using dUTP instead of deoxythymidine 5'-triphosphate (hereinafter, referred to as "dTTP"), treating a sample with heat-labile uracil-DNA glycosylase specifically cleaving DNA containing deoxyuridine 5'-monophosphate (dUMP), and performing a general PCR (see, Longo, M. C. et al., 1990, *Gene* 93, 125-128). Thus, a DNA polymerase catalyzing a PCR reaction in a mixture containing dUTP and having proofreading activity may be very useful. It has been known that among commonly used and commercially available DNA polymerases, T. aquaticus YT-1 DNA polymerase (hereinafter, referred to as "Taq DNA polymerase") not having proofreading activity enables PCR in the presence of dUTP, but *P. furiosus* DNA polymerase (hereinafter, referred to as "Pfu DNA polymerase") having proofreading activity and mainly used in PCR for diagnostic purposes does not enable PCR in the presence of dUTP (see, Hogrefe, H. H. et al., 2002, *Proc. Natl. Acad. Sci. USA* 99, 596-601).

The active Neq DNA polymerase prepared by the present method may be provided as a PCR kit along with PCR primers, dNTP, and the like. The active Neq DNA polymerase of the present invention or a PCR kit containing the same may be useful in genetic engineering and molecular biology experiments, clinical diagnosis and forensic medicine.

A better understanding of the present invention may be obtained through the following examples which are set forth for illustration. However, it will be apparent to those skilled in the art that these examples are not to be construed as the limit of the present invention.

EXAMPLE 1

Analysis of Nucleotide Sequences and Deduced Amino Acid Sequences of Neq DNA Polymerase-Encoding Genes The genomic sequence of *N. equitans* (GenBank accession number AE017199) was obtained from the homepage of the National Center for Biotechnology Information (NCBI), from which the previously reported complete genomic sequence of *N. equitans* (see, Waters, E. et al., 2003, *Proc. Natl. Acad. Sci. USA* 100, 12984-12988) is available. The nucleotide sequences of the two separate genes coding for Neq DNA polymerase and amino acid sequences deduced from the nucleotide sequences were analyzed using sequence analysis software, DNASIS (Hitachi Software Engineering Co., Japan) and PCGENE (Intelligenetics Co., USA). As a result, the large gene coding for Neq L was found to consist of an extein-coding region for the N-terminal part of Neq DNA polymerase, which consists of 578 amino acid residues, and an intein-coding region for the N-terminal part of a split mini-intein participating in protein trans-splicing, which consists of 98 amino acid residues. The small gene coding for Neq S was found to consist of an intein-coding region for the C-terminal part of the split mini-intein, which consists of 30 amino acid residues, and an extein-coding region for the C-terminal part of Neq DNA polymerase, which consists of 223 amino acid residues (see, panel A, FIG. 1). In addition, the extein-coding regions of the two genes were found to correspond to the complete sequence of an archaeal thermostable B-type DNA polymerase when sequentially linked. The calculated molecular masses of the N-terminal extein, consisting of 578 amino acid residues, and the C-terminal extein, consisting of 223 amino acid residues, were 68,405 daltons (hereinafter, referred to as "Da") and 26,041 Da, respectively; if added together, these would give a molecular mass very similar to that of other archaeal thermostable B-type DNA polymerases. Panel A of FIG. 1 shows a schematic gene map of the Neq DNA polymerase genes on the *N. equitans* genome, and the structures of polypeptides made from the genes. In panel A of FIG. 1, arrows on the *N. equitans* genome indicate the location on the genome and the direction of expression of Neq DNA polymerase genes. Polypeptides made from the genes, Neq L and Neq S, are shown in an N- to C-terminal direction. The words 'Ext-N', 'Int-N', 'Int-C' and 'Ext-C' indicate the extein of Neq L, the intein of Neq L, the intein of Neq S, and the extein of Neq S, respectively.

The deduced amino acid sequences of the exteins comprising Neq DNA polymerase were compared with amino acid sequences of already known archaeal thermostable B-type DNA polymerases using a computer program, MultAlin. As a result, Neq DNA polymerase was found to contain all of the highly conserved motifs among archaeal thermostable B-type DNA polymerases, six 5'→3' polymerase motifs which are important in DNA polymerization activity (see, Braithwaite, D. K. & Ito, J., 1993, *Nucleic Acids Res.* 21, 787-802), three 3'→5' exonuclease motifs which are important in proofreading activity (see, Blanco, L. et al., 1991, *Gene* 100, 27-38), and a DNA-binding motif (see, Truniger, V. et al., 1996,

*EMBO J.* 15, 3430-3441). The three 3'→5' exonuclease motifs and DNA-binding motif were present in the extein of Neq L, and the six 5'→3' polymerase motifs were distributed in the exteins of Neq L and Neq S (see, Panel A, FIG. 2). In addition, *M. thermautotrophicus* B-type DNA polymerase (hereinafter, referred to as "Mth DNA polymerase"), which is the only one encoded by two separate genes except for Neq DNA polymerase, was split outside the Pol I motif while avoiding the highly conserved motifs. In contrast, Neq DNA polymerase was split inside the highly conserved motif Pol I (see, Panel A, FIG. 2). Neq DNA polymerase showed 32.6% amino acid sequence similarity to split Mth DNA polymerase, which is encoded by two separate genes but is active as a dimer because it lacks an intein (see, Smith, D. R. et al., 1997, *J. Bacteriol.* 179, 7135-7155), and 36.6% amino acid sequence similarity to Pfu DNA polymerase, which is encoded by one gene (see, Uemori, T. et al., 1993, *Nucleic Acids Res.* 21, 259-265). Panel A of FIG. 2 shows a multiple sequence alignment in which the amino acid sequence of extein of Neq DNA polymerase are compared with those of other archaeal thermostable B-type DNA polymerases. In panel A of FIG. 2, Neq, Mth and Pfu indicate Neq DNA polymerase, Mth DNA polymerase and Pfu DNA polymerase, respectively, identical amino acids between Neq DNA polymerase and other DNA polymerases are indicated by stippled boxes, and the highly conserved motifs among archaeal thermostable B-type DNA polymerases and the position of the split are marked.

The deduced amino acid sequences of inteins comprising the split mini-intein of Neq DNA polymerase were compared with the amino acid sequence of the split mini-intein of Ssp DnaE protein (see, Wu, H. et al., 1998, *Proc. Natl. Acad. Sci. USA* 95, 9226-9231) using a computer program, MultAlin. As a result, the split mini-intein of Neq DNA polymerase contains all four blocks containing amino acid residues critical for self-splicing (see, Pietrokovski, S., 1998, *Protein Sci.* 7, 64-71). The A and B blocks were present in the intein of Neq L, and the F and G blocks were present in the intein of Neq S (see, Panel B, FIG. 2). The panel B of FIG. 2 shows a sequence alignment in which the amino acid sequence of intein of Neq DNA polymerase is compared with that of intein of Ssp DnaE protein. In panel B of FIG. 2, Neq and Ssp indicate the split mini-intein of Neq DNA polymerase and the split mini-intein of Ssp DnaE protein, respectively, identical amino acids between both split mini-inteins of Neq DNA polymerase and Ssp DnaE protein are indicated by stippled boxes, and blocks for the self-splicing and the position of the split are marked.

EXAMPLE 2

Construction of Recombinant Plasmids

Recombinant plasmids prepared by inserting each of the two genes encoding Neq DNA polymerase into an expression vector, a recombinant plasmid prepared by inserting the two genes into one expression vector, and recombinant plasmids prepared by sequentially linking only extein-coding regions and inserting them into an expression vector were constructed as follows (see, Panel B, FIG. 1). Panel B of FIG. 1 shows recombinant plasmid constructs for expressing the genes. In panel B of FIG. 1, $P_{T7lac}$ and $His_6$ indicate a T7lac promoter and a C-termial $His_6$-tag, respectively, the extein of Neq L, the intein of Neq L, the intein of Neq S, and the extein of Neq S are marked as in panel A of FIG. 1, and only regions expressed along with the promoter region of the expression vector pET-22b(+) are shown.

1. Based on the nucleotide sequence of the large gene encoding Neq L, primers were designed in a manner complementary to the 5'-end and 3'-end. The 5'-end primer NPOL1FN (5'-ATTATAGCATATGTTACACCAACTC-CCCACG-3' (SEQ ID NO:1)) was synthesized in a length of 31bases containing an NdeI cleavage site (5'-CATATG-3') having a start codon (ATG). The primer complementary to the 3'-end, NPOL1RX (3'-CGGTTCCTTATACTTTTATTTT-TATTAGAGCTCTCTA-5'(SEQ ID NO:2)), was synthesized in a length of 37 bases containing a XhoI cleavage site (5'-CTCGAG-3') not having a stop codon in order to be expressed together with the carboxy-terminal $His_6$-tag of the expression vector, which is useful upon protein purification. Then, PCR was carried out using the *N. equitans* genomic DNA, which was kindly provided by the research group that first isolated the *N. equitans* strain, as a template in order to amplify the Neq L-coding gene. A PCR reaction mixture excluding Pfu DNA polymerase (0.1 μg *N. equitans* genomic DNA, 5 pmole 5'-end primer and 3'-end primer, 200 μM dNTP, 1× Pfu DNA polymerase reaction buffer) was heated to 100° C. for 5 min to denature the genomic DNA, rapidly cooled on ice, supplemented with 2.5 units of Pfu DNA polymerase, and subjected to a PCR. PCR conditions included 30 cycles of three steps: DNA denaturation at 94° C. for 1 min, primer annealing at 58° C. for 1 min, and DNA extension at 72° C. for 5 min. The PCR reaction mixture was then electrophoresed on an agarose gel along with a DNA size marker, and a band was found at about two kilobases (hereinafter, referred to as "kb"). In order to extract the amplified DNA fragment, the PCR reaction mixture was treated with the equal volume of TE-saturated phenol and then chloroform/isoamylalcohol (24:1), and was recovered by ethanol precipitation. The recovered DNA fragment was digested with NdeI and XhoI, electrophoresed on an agarose gel along with a DNA size marker, and extracted from the agarose gel using a gel extraction kit (Qiagen GmbH, Germany). The extracted, restriction enzyme-digested DNA fragment containing the Neq L-coding gene was inserted into the expression vector pET-22b(+), which was digested with the same restriction enzyme, using T4 DNA ligase. The resulting vector was transformed into *E.coli* BL21-Codon-Plus(DE3)-RIL by electroporation (see, Sambrook, J. et al., 1989, *Molecular Cloning: a Laboratory Manual*, 2nd ed., Cold Spring Harbor Laboratory Press). Thereafter, plasmid DNA was isolated from the transformed cells using an alkaline lysis method, digested with NdeI and XhoI, and electrophoresed on an agarose gel along with a DNA size marker in order to select a transformant into which the DNA fragment containing the Neq L-coding gene was successfully introduced. Also, the plasmid DNA from the selected transformant was sequenced, and it was confirmed that the Neq L-coding gene was accurately inserted into the expression vector. The recombinant plasmid thus constructed for expressing the Neq L-coding gene was designated "pENPLX" (see, Panel B, FIG. 1), and the *E.coli* BL21-CodonPlus(DE3)-RIL transformed with the recombinant plasmid pENPLX was designated "*E.coli* BL21-CodonPlus(DE3)-RIL/pENPLX".

2. Based on the nucleotide sequence of the small gene encoding Neq S, primers were designed in the manner complementary to the 5'-end and 3'-end. The 5'-end primer NPOL2FN (5'-TAATTACATATGCGCTATCTTG-GCAAAAAGAG-3' (SEQ ID NO:3)) was synthesized in a length of 33 bases containing an NdeI cleavage site having a start codon. The primer complementary to the 3'-end, NPOL2RAB (3'-GTTTTTTGATTGTCTAAAGAAATT-TACTATTCTTCCTCTATATTAATTACCTAGGGC-5' (SEQ ID NO:4)), was synthesized in a length of 57 bases containing a sequence (5'-CTCCTTC-3') complementary to the Shine- Dalgarno sequence (5'-GAAGGAG-3') (see, Shine, J. & Dalgarno, L., 1975, *Nature* 254, 34-38), an AseI cleavage site (5'-ATTAAT-3'), and a BamHI cleavage site (5'-GGATCC-3'). Then, PCR was carried out using the *N. equitans* genomic DNA as a template and the NPOL2FN and NPOL2RBA primers. According to the same method as described above, the amplified DNA fragment of about 760 bp, which contained the Neq S-coding gene, was then inserted into the NdeI/BamHI sites of the expression vector pET-22b(+), and the vector was transformed into *E.coli* BL21-CodonPlus (DE3)-RIL. The recombinant plasmid thus constructed for expressing the Neq S-coding gene was designated "pENPS" (see, Panel B, FIG. 1), and the *E. coli* BL21-CodonPlus (DE3)-RIL transformed with the recombinant plasmid pENPS was designated "*E. coli* BL21-CodonPlus(DE3)-RIL/pENPS".

3. A recombinant plasmid carrying both genes coding for Neq DNA polymerase was constructed as follows. First, a primer complementary to the 3'-end of the Neq L-coding gene was designed. The 3'-end-complementary primer NPOL1RB (3'-GGTTCCTTATACTTTTATTTTTATTAAT-TACTCCTAGGGC-5' (SEQ ID NO:5)) was 40 bases long and contained a stop codon and a BamHI cleavage site. Then, PCR was carried out using the *N. equitans* genomic DNA as a template and the NPOL1FN and NPOL1RB primers. According to the same method as described above, the amplified DNA fragment containing the Neq L-coding gene was digested with NdeI and BamHI, inserted into the AseI/BamHI sites (NdeI and AseI have compatible cohesive ends) of the recombinant plasmid pENPS, into which the Neq S-coding gene was inserted, and introduced into *E. coli* BL21-CodonPlus(DE3)-RIL. The thus constructed recombinant plasmid for co-expressing the two genes coding for Neq L and Neq S, which sequentially carried the Neq S-coding gene, the Shine-Dalgarno sequence and the Neq L-coding gene, was designated "pENPC" (see, Panel B, FIG. 1), and the *E. coli* BL21-CodonPlus (DE3)-RIL transformed with the recombinant plasmid pENPC was designated "*E. coli* BL21-CodonPlus (DE3)-RIL/pENPC".

The *E. coli* BL21-CodonPlus(DE3)-RIL harboring the recombinant vector pENPC (*Escherichia coli* BL21-CodonPlus(DE3)-RIL/pENPC) was deposited at the Korean Agricultural Culture Collection (Seodun-dong, Gwonseon-gu, Suwon Gyeonggi-do, Republic of Korea) on Sep. 21, 2005, and assigned accession number KACC95038P.

Morever the above *E. coli* BL21-CodonPlus(DE3)-RIL harboring the recombinant vector pENPC was deposited at the Korean Culture Center of Microorganisms on Sep. 22, 2006, and assigned accession number KCCM10780P.

4. In order to construct a recombinant plasmid into which only extein-coding regions which are sequentially-linked, except for the intein-coding regions from the two genes encoding Neq DNA polymerase, are inserted, a primer complementary to the 3'-end of the extein-coding region of Neq L was newly designed. The 3'-end-complementary primer NPOL1PR (3'-CTTCCTAAGTTTCATTAAATAC-CTCTATGGCTAAGTAAT-5'(SEO ID NO:6)) was 39 bases long and contained 12 bases complementary to the 5'-end of the extein-coding region of Neq S. Then, PCR was carried out using the *N. equitans* genomic DNA as a template and the NPOL1FN and NPOL1PR primers. The amplified DNA fragment containing the extein-coding region of Neq L was electrophoresed on an agarose gel along with a DNA size marker, and extracted from the agarose gel using a DNA extraction kit. In addition, a primer complementary to the 5'-end of the extein-coding region of Neq S was newly designed. The 5'-end primer NPOL2PF (5'-ATTTATG-GAGATACCGATTCATTATTCATTTCTGGGG-3' (SEQ ID NO:7)) was 37 bases long and contained 12 bases complementary to the 3'-end of the extein-coding region of Neq L. Then, PCR was carried out using the *N. equitans* genomic DNA as a template and the NPOL2PF and NPOL2RAB primers. The amplified DNA fragment containing the extein-coding region of Neq S was electrophoresed on an agarose gel along with a DNA size marker, and extracted from the agarose gel using a DNA extraction kit. Thereafter, PCR was carried out using the two recovered DNA fragments each containing the extein coding regions of Neq L and Neq S as templates and the NPOL1FN and NPOL2RAB primers. According to the same method as described above, the Neq P-coding gene of about 2.4 kb was inserted into the NdeI/BamHI sites of the expression vector pET-22b(+), and introduced into *E. coli* BL21-CodonPlus (DE3)-RIL. The thus constructed recombinant plasmid for expressing the Neq P-coding gene was designated "pENPP" (see, Panel B, FIG. 1), and the *E. coli* BL21-CodonPlus(DE3)-RIL transformed with the recombinant plasmid pENPP was designated "*E. coli* BL21-CodonPlus(DE3)-RIL/DENPP".

The *E. coli* BL21-CodonPlus(DE3)-RIL harboring the recombinant vector pENPP (*Escherichia coli* BL21-CodonPlus(DE3)-RIL/pENPP) was deposited at the Korean Agricultural Culture Collection (Seodun-dong, Gwonseon-gu, Suwon Gyeonggi-do, Republic of Korea) on Sep. 21, 2005, and assigned accession number KACC95039P.

Moreover, the above *E. coli* BL21-CodonPlus(DE3)-RIL harboring the recombinant vector pENPP was deposited at the Korean Culture Center of Microorganisms on Sep. 22, 2006, and assigned accession number KCCM10781P.

EXAMPLE 3

Protein Expression and Purification

The *E. coli* BL21-CodonPlus(DE3)-RIL transformants harboring the recombinant plasmids constructed in Example 2 were pre-cultured in 3 ml of LB broth supplemented with 100 μg/ml ampicillin and 34 μg/ml chloramphenicol at 37° C. overnight. The seed culture was inoculated in 50 ml of LB broth supplemented with 100 μg/ml ampicillin and incubated at 37° C. When the culture reached an optical density at 600 nm of about 0.6, IPTG was added to the medium in a final concentration of 0.5 mM to induce expression of the cloned genes, and cells were further cultured for 5 hrs at 37° C. Cells were harvested by centrifugation and resuspended in buffer A (20 mM Tris-HCl, pH 7.4, and 50 mM NaCl) containing 1 mM phenylmethylsulfonyl fluoride (hereinafter, referred to as "PMSF"). The resuspended cells were disrupted by sonication and centrifuged to obtain supernatants and pellets. The protein samples were analyzed using sodium dodecyl sulfate-polyacrylamide gel electrophoresis (SDS-PAGE). Neq L and Neq P were found to be expressed as soluble proteins. Neq S was expressed as an insoluble protein in the *E. coli* BL21-CodonPlus(DE3)-RIL carrying the recombinant plasmid pENPS, but was expressed as a soluble protein when expressed together with Neq L in *E. coli* BL21-CodonPlus (DE3)-RIL carrying the recombinant plasmid pENPC.

In order to determine whether the heat treatment could be used to eliminate *E. coli* proteins upon the purification of proteins expressed by IPTG induction in *E. coli* BL21-CodonPlus(DE3)-RIL carrying the recombinant plasmids pENPC and pENPP, the sonicated extracts were incubated at 80° C. for 30 min and subjected to SDS-PAGE. As a result, the polypeptides co-expressed in the *E. coli* BL21-CodonPlus (DE3)-RIL carrying the recombinant plasmids pENPC, Neq L and Neq S, was interestingly spliced to remove inteins by protein trans-splicing during the heat treatment, and only exteins were ligated to form a single polypeptide chain, Neq C (see, FIG. 3), indicating that heat treatment could be used for the purification of Neq C and Neq P. FIG. 3 shows the result of protein trans-splicing of the co-expressed Neq L and Neq S in *E. Coli* BL21-CodonPlus(DE3)-RIL harboring the recombinant plasmid pENPC according to heat treatment time. In FIG. 3, when the amount of Neq L and Neq S co-expressed by IPTG induction decreased, the protein trans-slicing product, Neq C, and the cleavage product of Neq L, Ext-N (the extein of Neq L), increased. Lane U shows the sonicated extract of uninduced *E. coli* BL21-CodonPlus (DE3)-RIL cells carrying the recombinant plasmid pENPC, and lane M shows a low molecular mass marker.

Figure 4:
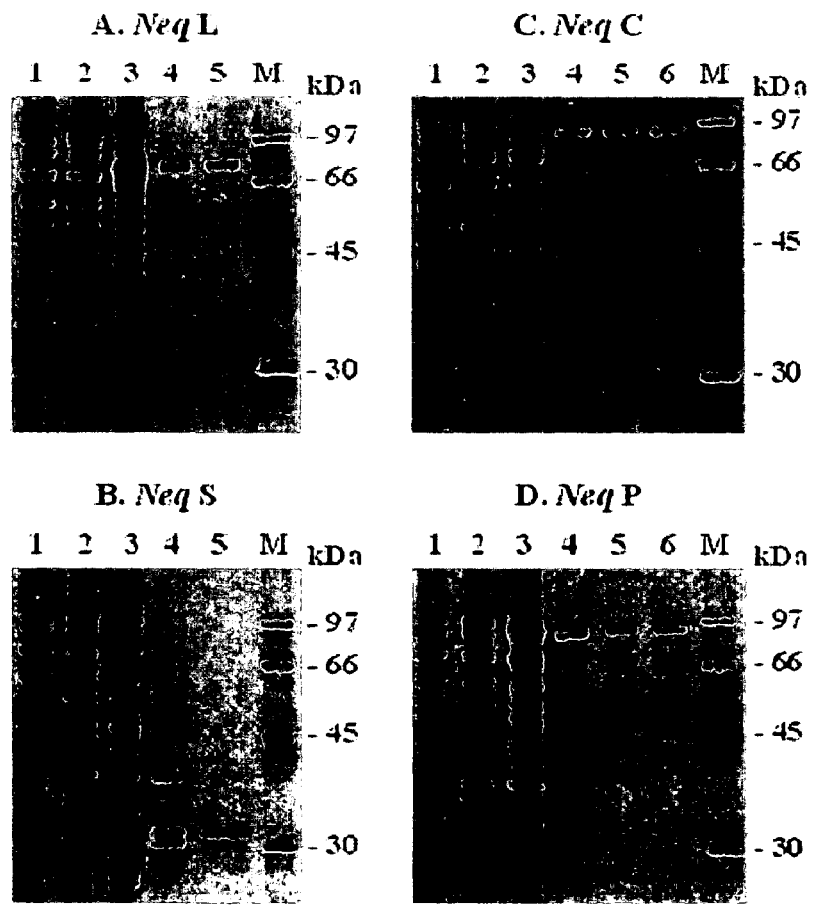
FIG. 4 shows the results of SDS-PAGE of Neq L, Neq S, Neq C and Neq P proteins at each purification step.

In order to purify the successfully expressed proteins, the *E. coli* BL21-CodonPlus(DE3)-RIL transformants harboring the recombinant plasmids were pre-cultured in 30 ml of LB broth supplemented with 100 μg/ml ampicillin and 34 μg/ml chloramphenicol at 37° C. overnight. The seed culture was inoculated in a 1% concentration in 2 liters of LB broth supplemented with 100 μg/ml ampicillin, and incubated at 37° C. When the culture reached an optical density at 600 nm of about 0.6, IPTG was added to the medium in a final concentration of 0.5 mM, and cells were further cultured for 5 hrs at 37° C. Cells were harvested by centrifugation and resuspended in buffer A containing 1 mM PMSF. The resuspended cells were disrupted by sonication and centrifuged. Each protein was then purified as described below. 1̂ Neq L was purified using the nature of the His$_6$-tagged protein. The sonicated extract containing Neq L expressed by IPTG induction was dialyzed against buffer B (20 mM Tris-HCl, pH 7.4, and 500 mM NaCl), and was then applied onto a HiTrap™ Chelating HP column (Amersham Biosciences, Sweden), which is an affinity column for purifying a His$_6$-tagged protein, in order to eliminate most undesired proteins. Major fractions containing Neq L were pooled and dialyzed against buffer A. Neq L was further purified using a UNO™ Q column (Bio-Rad Laboratories, USA), which is an anion-exchange column. Fractions containing purified Neq L were pooled, dialyzed against buffer A, and stored at 4° C. The molecular mass of the purified Neq L was determined by sodium dodecyl sulfate-polyacrylamide gel electrophoresis (SDS-PAGE), and found to be 79,000 Da, which was in good agreement with the molecular mass calculated from the deduced amino acid sequence, 79,864 Da (see, Panel A, FIG. 4). Panel A of FIG. 4 shows the results of SDS-PAGE of Neq L at each purification step. In panel A of FIG. 4, each lane is as follows: lane 1, sonicated extract of *E. coli* BL21-CodonPlus(DE3)-RIL cells; lane 2, sonicated extract of uninduced *E. coli* BL21-CodonPlus(DE3)-RIL cells harboring the recombinant plasmid pENPLX; lane 3, sonicated extract of IPTG-induced *E. coli* BL21-CodonPlus(DE3)-RIL cells harboring the recombinant plasmid pENPLX; lane 4, Neq L-containing fractions collected by HiTrap™ Chelating HP column chromatography; lane 5, purified Neq L-containing fractions collected by UNO™ Q column chromatography; lane M, low molecular mass marker.

2̂ Neq S was purified in the presence of urea because it was expressed as an insoluble protein when expressed alone. The sonicated pellet containing Neq S expressed by IPTG induction was resuspended in buffer C (20 mM Tris-HCl, pH 7.4, and 8 M urea) containing 1.5 M ammonium sulfate, and was then loaded onto a HiTrap™ Phenyl FF column (Amersham Biosciences, Sweden), which is a hydrophobic interaction column, in order to completely purify Neq S. Fractions containing the purified Neq S were pooled, dialyzed against buffer A, and stored at 4° C. The molecular mass of the purified Neq S was determined by SDS-PAGE, and found to be 30,500 Da, which was in good agreement with the molecular mass calculated from the deduced amino acid sequence, 29,538 Da (see, Panel B, FIG. 4). Panel B of FIG. 4 shows the results of SDS-PAGE of Neq S at each purification step. In panel A of FIG. 4, each lane is as follows: lane 1, sonicated extract of *E. coli* BL21-CodonPlus(DE3)-RIL cells; lane 2, sonicated extract of uninduced *E. coli* BL21-CodonPlus(DE3)-RIL cells harboring the recombinant plasmid pENPS; lane 3, sonicated extract (centrifugal supernatant) of IPTG-induced *E. coli* BL21-CodonPlus(DE3)-RIL cells harboring the recombinant plasmid pENPS; lane 4, sonicated pellet (centrifugal pellet) of IPTG-induced *E. coli* BL21-CodonPlus(DE3)-RIL cells harboring the recombinant plasmid pENPS; lane 5, purified Neq S-containing fractions collected by HiTrap™ Phenyl FF column chromatography; lane M, low molecular mass marker.

3̂ Neq C and 4̂ Neq P were purified according to the same procedure by heat treatment. The sonicated extract containing Neq L and Neq co-expressed by IPTG induction using the recombinant plasmid pENPC and the sonicated extract containing Neq P expressed by IPTG induction using the recombinant plasmid pENPP were individually incubated at 80° C. for 30 min in order to eliminate the majority of the heat-labile *E. coli* proteins. During the heat treatment, the co-expressed proteins, Neq L and Neq S, were spliced, and a trans-spliced protein (Neq C) was identified. After the heat-treated samples were centrifuged, the supernatants were dialyzed against buffer A, and were then applied onto a UNO™ Q column, which is an anion exchange column, and an UNO™ S column, which is a cation-exchange column (Bio-Rad Laboratories Inc., USA), in order to completely purify Neq C and Neq P. Fractions containing the purified Neq C and Neq P were pooled, dialyzed against buffer A, and stored at 4° C. The molecular masses of the purified Neq C (Panel C, FIG. 4) and Neq P (Panel D, FIG. 4) were determined using SDS-PAGE, and both were found to be 94,000 Da, which was in good agreement with the molecular mass calculated from the deduced amino acid sequence, 94,427 Da. Panel C of FIG. 4 shows the results of SDS-PAGE of Neq C at each purification step, and panel D of FIG. 4 shows the results of SDS-PAGE of Neq P at each purification step. In panels C and D of FIG. 4, each lane is as follows: lane 1, sonicated extract of *E. coli* BL21-CodonPlus(DE3)-RIL cells; lane 2, sonicated extract of uninduced *E. coli* BL21-CodonPlus(DE3)-RIL cells harboring the recombinant plasmid pENPC or pENPP; lane 3, sonicated extract of IPTG-induced *E. coli* BL21-CodonPlus(DE3)-RIL cells harboring the recombinant plasmid PENPC or pENPP; lane 4, supernatant of sample incubated at 80° C. for 30 min; lane 5, Neq C or Neq P-containing fractions collected through UNO™ Q column chromatography; lane 6, purified Neq C or Neq P-containing fractions collected using UNO™ S column chromatography; lane M, low molecular mass marker.

EXAMPLE 4

Protein Trans-Splicing Assay

Figure 5:
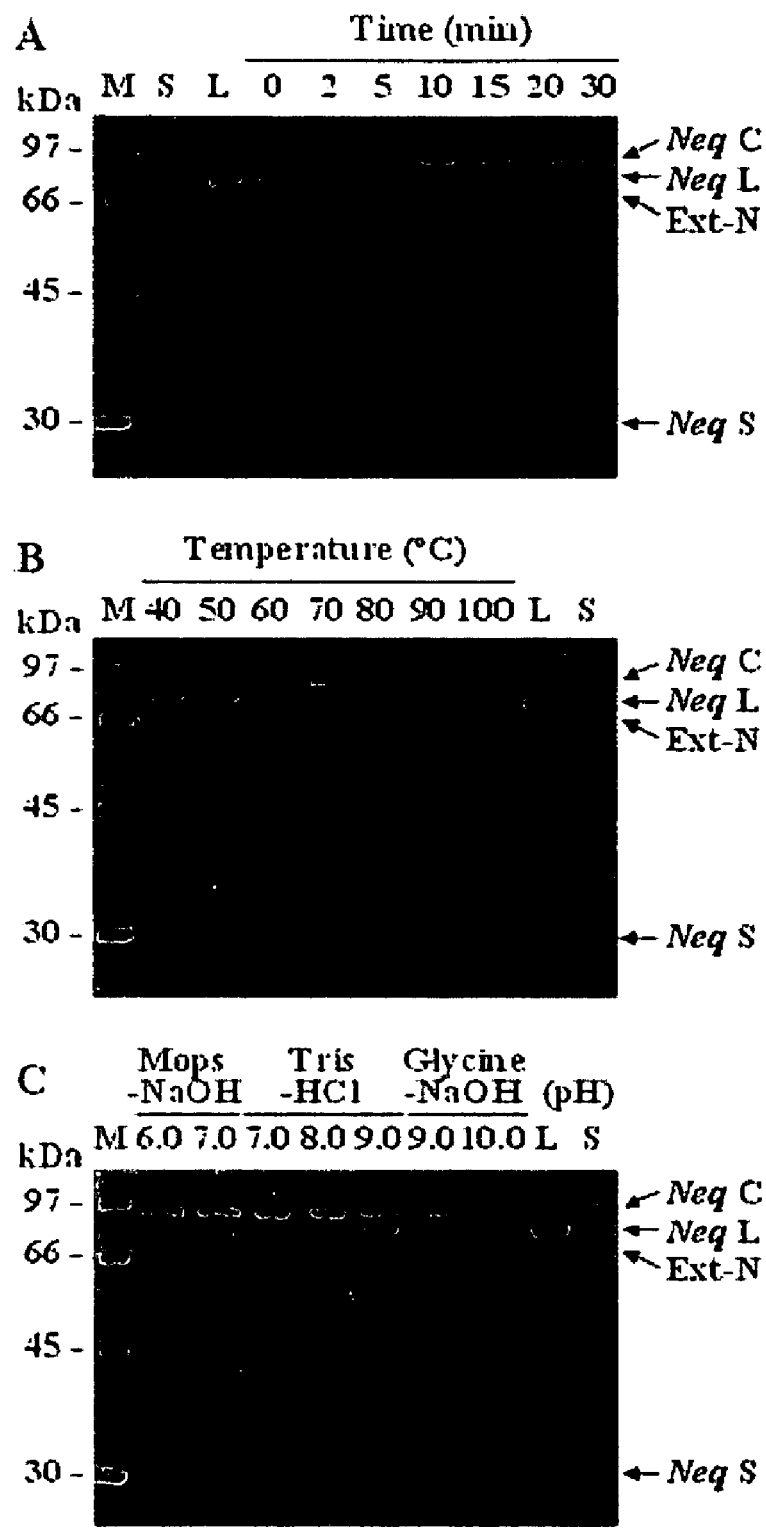
FIG. 5 shows the results of protein trans-splicing of the purified Neq L and Neq S according to reaction time, temperature and pH.

In order to confirm the protein trans-splicing required for the preparation of a single complete Neq DNA polymerase at the protein level, the Neq L and Neq S (100 pmol each) purified in Example 3 were individually incubated in protein trans-splicing reaction buffer (20 mM Tris-HCl, pH 8.0, 50 mM NaCl) at 80° C. for 30 min, and were analyzed using SDS-PAGE. As a result, consistent with the results of protein trans-splicing of the Neq L and Neq S co-expressed in *E. coli* BL21-CodonPlus(DE3)-RIL carrying the recombinant plasmid pENPC according to heat treatment time, the protein trans-slicing product, Neq C, and the cleavage product of Neq L, Ext-N, were found to increase when the amount of purified Neq L and Neq S added to the reaction mixture decreased. Compared to the protein trans-splicing using the co-expressed Neq L and Neq S, which were expressed in different levels, the protein trans-splicing using equal amounts of the purified Neq L and Neq S was found to produce higher levels of Neq C and lower levels of Ext-N (see, Panel A, FIG. 5). Panel A of FIG. 5 shows the results of protein trans-splicing of the purified Neq L and Neq S according to reaction time. In panel A of FIG. 5, each lane is as follows: lane L, 100 pmole of purified Neq L; lane S, 100 pmole of purified Neq S; and lane M, low molecular mass marker.

In order to investigate the effect of temperature on protein trans-splicing, the reaction mixtures were incubated at 40-100° C. for 30 min and analyzed using SDS-PAGE. As a result, protein trans-splicing was found to occur at more than 50° C. and to be maximal at 80° C. (see, Panel B, FIG. 5). Panel B of FIG. 5 shows the results of protein trans-splicing of the purified Neq L and Neq S according to reaction temperature. In panel B of FIG. 5, each lane is as follows: lane L, 100 pmole of purified Neq L; lane S, 100 pmole of purified Neq S; and lane M, low molecular mass marker.

In order to investigate the effect of pH on protein trans-splicing, the reaction mixtures were prepared using 50 mM buffer at a pH ranging from 6.0 to 10.0 (50 mM Mops-NaOH buffer of pH 6.0-7.0, 50 mM Tris-HCl buffer of pH 7.0-9.0, 50 mM Glycine-NaOH buffer of pH 9.0-10.0) instead of 20 mM Tris-HCl (pH 8.0) buffer. The reaction mixtures were incubated at 80° C. for 30 min and analyzed using SDS-PAGE. As a result, protein trans-splicing was found to highly occur at pH 6.0-9.0, but seldom occurred at pH 10.0 (see, Panel C, FIG. 5). Panel C of FIG. 5 shows the results of protein trans-splicing of the purified Neq L and Neq S according to reaction pH. In panel C of FIG. 5, each lane is as follows: lane L, 100 pmole of purified Neq L; lane S, 100 pmole of purified Neq S; and lane M, low molecular mass marker.

EXAMPLE 5

DNA Polymerization Activity Assay

The DNA polymerase activity of the proteins purified in Example 3 was measured as follows (see, Choi, J. J. & Kwon, S.-T., 2004, *J. Microbiol. Biotechnol.* 14, 1022-1030). A basic reaction mixture (50 μp1) contained 1.25 μg of activated calf thymus DNA, 20 mM Tris-HCl (pH 7.5), 2 mM $MgCl_2$, 40 mM KCl, 100 μM of deoxyadenosine 5'-triphosphate (hereinafter, referred to as "dATP"), 100 μM of deoxycytidine 5'-triphosphate (hereinafter, referred to as "dCTP"), 100 μM of deoxyguanosine 5'-triphosphate (hereinafter, referred to as "dGTP"), 10 μM of dTTP, and 0.5 μCi of [methyl-$^3$H]thymidine 5'-triphosphate. The reaction mixture was incubated at 75° C. for 10 min, and was then rapidly cooled on ice. The reaction mixture was spotted onto a DE81 filter paper disc (23 mm, Whatman, UK). The DE81 filter paper disc was dried at 65° C., and washed in 0.5 M sodium phosphate (pH 7.0) buffer for 10 min and in 70% ethanol for 5 min, then dried at 65° C. The DNA polymerase activity was measured by counting incorporated radioactivity of the dried DE81 filter paper disc using a Beckman LS6500 scintillation counter (Beckman Co., USA). As a result of the measurement of the DNA polymerization activity of the four purified proteins, Neq S and Neq L were found not to have DNA polymerization activity. In contrast, a single complete Neq DNA polymerase prepared at the protein level, Neq C (the co-expressed polypeptides not having DNA polymerization activity alone, Neq L and Neq S, were spliced by protein trans-splicing and purified as a single protein having DNA polymerization activity), and Neq P prepared at the gene level (expressed as a single protein having DNA polymerization activity from a gene encoding a protein in a spliced form, the gene being prepared by genetic recombination using PCR, and purified) were found to be active Neq DNA polymerases having DNA polymerization activity. These results were consistent with the results of amino acid sequence analysis, which showed that the six 5'→3' polymerase motifs, which are critical in DAN polymerization activity, are distributed in the exteins of Neq L and Neq S.

In addition, the DNA polymerization activity of Neq C and Neq P was measured under various conditions as described below in order to investigate the biochemical properties of the proteins with respect to DNA polymerization activity. The active Neq DNA polymerases, Neq C and Neq P, which had the same amino acid sequence, were found to be, as expected, identical enzymes exhibiting the same biochemical properties.

Figure 6:
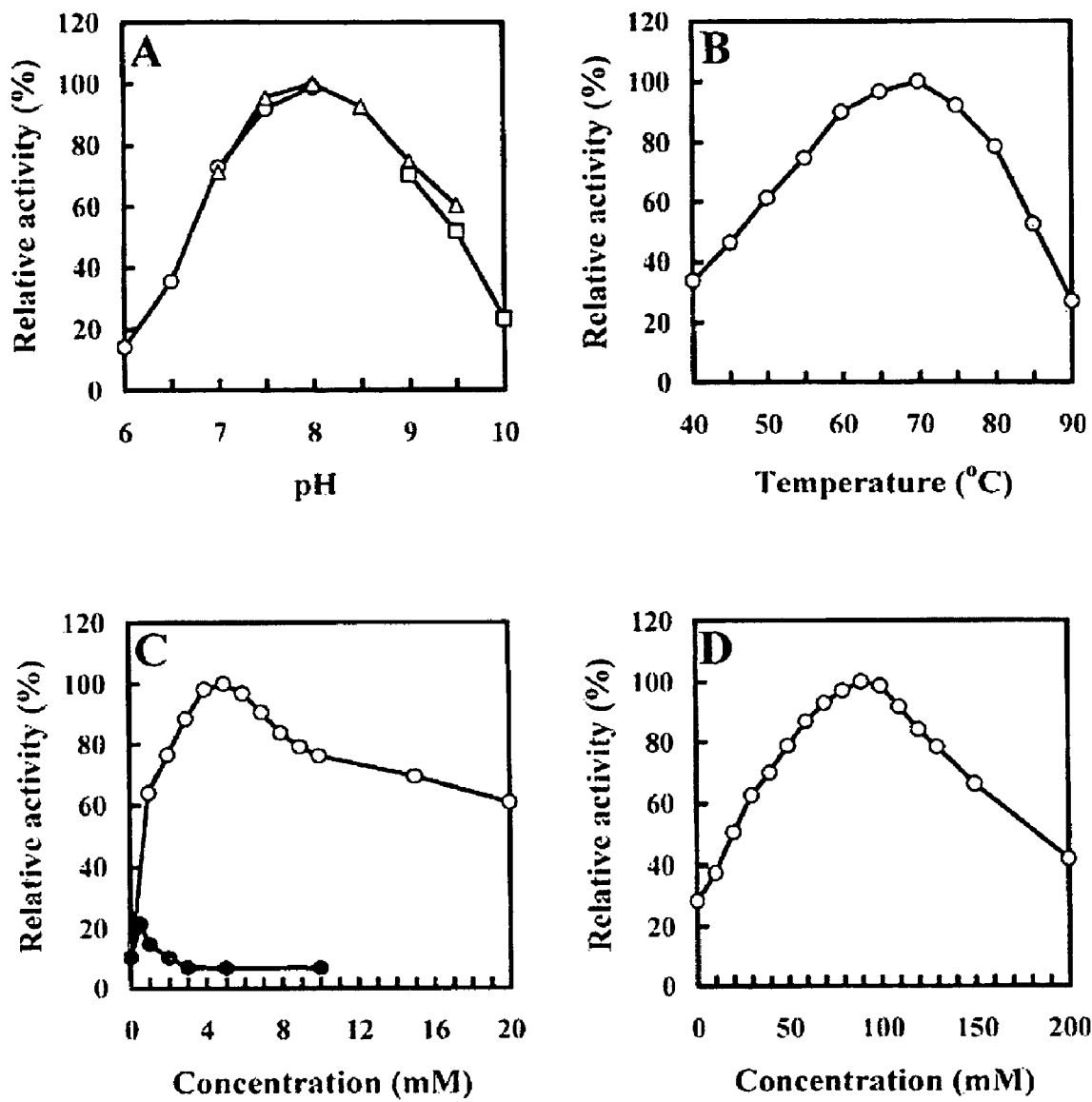
FIG. 6 shows the biochemical properties of active Neq DNA polymerase with respect to DNA polymerization activity.

In order to investigate the effect of pH on the DNA polymerization activity of active Neq DNA polymerase, the DNA polymerization activity was measured as described above using 50 mM buffer at a pH ranging from 6.0 to 10.0 (50 mM Mops-NaOH buffer of pH 6.0-8.0, 50 mM Tris-HCl buffer of pH 7.0-9.5, 50 mM Glycine-NaOH buffer of pH 9.0-10.0) instead of 20 mM Tris-HCl (pH 7.5) buffer. As a result, the active Neq DNA polymerase displayed maximal activity at pH 8.0 (see, Panel A, FIG. 6). The panel A of FIG. 6 shows the effect of pH on the DNA polymerization activity of active Neq DNA polymerase. In panel A of FIG. 6, an open circle (○), an open triangle (Δ) and an open square (□) show the results of measurement with 50 mM Mops-NaOH buffer, 50 mM Tris-HCl buffer and 50 mM Glycine-NaOH buffer, respectively.

In order to investigate the effect of temperature on the DNA polymerization activity of active Neq DNA polymerase, the DNA polymerization activity was measured at 40-90° C. as described above. As a result, the active Neq DNA polymerase displayed maximal activity at 70° C. (see, Panel B, FIG. 6). However, since the active Neq DNA polymerase was very stable even above 70° C., the temperature giving the maximal activity was considered to result from the denaturation of the activated calf thymus DNA, used as a substrate, at high temperature. Panel B of FIG. 6 shows the effect of temperature on the DNA polymerization activity of active Neq DNA polymerase.

In order to investigate the effect of divalent cations on the DNA polymerization activity of active Neq DNA polymerase, the DNA polymerization activity was measured at various concentrations of $MgCl_2$ or $MnCl_2$. As a result, the active Neq DNA polymerase displayed maximal activity at 5 mM magnesium ions ($Mg^{2+}$) (see, Panel C, FIG. 6). Panel C of FIG. 6 shows the effect of divalent cations on the DNA polymerization activity of active Neq DNA polymerase. In panel C of FIG. 6, an open circle (○) and a closed circle (●) show the results of the measurement with magnesium ions ($Mg^{2+}$) and manganese ions ($Mn^{2+}$).

In order to investigate the effect of KCl on the DNA polymerization activity of active Neq DNA polymerase, the DNA polymerization activity was measured at various concentrations of KCl. As a result, the active Neq DNA polymerase displayed maximal activity at 90-100 mM KCl (see, Panel D, FIG. 6). Panel D of FIG. 6 shows the effect of KCl on the DNA polymerization activity of active Neq DNA polymerase.

In order to investigate the thermostability of active Neq DNA polymerase, samples were collected at given time points during storage at 95° C. and 100° C. for 4 hrs, and were evaluated for DNA polymerization activity. As a result, the active Neq DNA polymerase was fairly stable during storage at 75° C. for 4 hrs, and had half-lives of 183 min at 95° C. and 62 min at 100° C. (see, FIG. 7). FIG. 7 shows the thermostability of active Neq DNA polymerase. In FIG. 7, an open circle (○) and a closed circle (●) show the results upon storage at 95° C. and 100° C., respectively.

EXAMPLE 6

Exonuclease Activity Assay

The exonuclease activity of the proteins purified in Example 3 was measured as follows (see, Choi, J. J. & Kwon, S.-T., 2004, *J. Microbiol. Biotechnol.* 14, 1022-1030). First, in order to prepare a DNA substrate labeled with a radioisotope at the 3'-end, pBluescript SK vector DNA digested with NotI was subjected to a filling-in reaction using Klenow fragment in the presence of α-$^{32}$P]dCTP. Also, in order to prepare a DNA substrate labeled with a radioisotope at the 5'-end, pBluescript SK vector DNA digested with NotI was phosphorylated using T4 polynucleotide kinase in the presence of [γ-$^{32}$P]ATP. The DNA substrates labeled with radioisotopes were purified using a Sephadex G-25 column. The reaction mixture (50 μl) then contained the DNA substrate labeled with a radioisotope at the 3'-end or 5'-end, 20 mM Tris-HCl (pH 7.5), 2 mM $MgCl_2$, 40 mM KCl, and 0.01% bovine serum albumin (hereinafter, referred to as "BSA"). The reaction mixture was incubated at 75° C. in the absence and presence of dNTP, and was then rapidly cooled on ice. The reaction mixture was mixed with 1 ml of 5% trichloroacetic acid and centrifuged. Using the supernatant, the exonuclease activity was measured by counting radioactivity using a Beckman LS6500 scintillation counter. As a result of the measurement of the 5'→3' exonuclease activity and the 3'→5' exonuclease activity, also known as proofreading activity, of the four purified proteins, Neq S lacked any detectable exonuclease activity, Neq L had only low proofreading activity, and the single complete active Neq DNA polymerases, Neq C and Neq P, had only high proofreading activity (see, Panel A, FIG. 8). These results were consistent with the results of amino acid analysis, which showed the presence of the three 3'→5' exonuclease motifs critical in proofreading activity within the extein of Neq L. The result, that the active Neq DNA polymerases having the same activity, Neq C and Neq P, have higher proofreading activity than Neq L, which has proofreading activity alone, indicates that the extein of Neq S does not affect the absence or presence of proofreading activity but affects the degree of proofreading activity. Panel A of FIG. 8 shows the 3'→5' exonuclease activity of Neq L and active Neq DNA polymerases over time. In panel A of FIG. 8, an open triangle (△), an open circle (○), a closed triangle (▲), and a closed circle (●) show the 3'→5' exonuclease activity of active Neq DNA polymerase in the presence of dNTPs, the 3'→5' exonuclease activity of active Neq DNA polymerase in the absence of dNTPs, the 3'→5' exonuclease activity of Neq L in the presence of dNTP, and the 3'→5' exonuclease activity of Neq L in the absence of dNTP, respectively. Total RA and Sol. RA indicate the radioactivity of the DNA substrate labeled with a radioisotope at the 3'-end, which was used in each reaction, and the radioactivity of the supernatant after the reaction, respectively.

In addition, the proofreading activity of Neq L, Neq C and Neq P was measured under various conditions as described below in order to investigate the biochemical properties of the proteins with respect to proofreading activity. Neq L exhibited biochemical properties different from those of Neq C and Neq P. Consistent with the results of the DNA polymerase activity assay, the active Neq DNA polymerases, Neq C and Neq P, were confirmed to be the same enzymes because they exhibited the same biochemical properties with respect to proofreading activity.

In order to investigate the effect of pH on the proofreading activity of Neq L and active Neq DNA polymerase, the proofreading activity was measured as described above using 50 mM buffer at a pH ranging from 6.5 to 9.5 (50 mM Mops-NaOH buffer of pH 6.5-8.0, 50 mM Tris-HCl buffer of pH 7.0-9.5, 50 mM Glycine-NaOH buffer of pH 9.0-9.5) instead of 20 mM Tris-HCl (pH 7.5) buffer in the absence of dNTPs. As a result, the active Neq DNA polymerase displayed maximal activity in Tris-HCl buffer at pH 9.0, and Neq L displayed maximal activity in Mops-NaOH buffer at pH 6.5 (see, Panel B, FIG. 8). Panel B of FIG. 8 shows the effects of pH on the 3'→5' exonuclease activity of Neq L and active Neq DNA polymerase. In panel B of FIG. 8, an open circle (○), an open triangle (△) and an open square (□) show the results of the 3'→5' exonuclease activity assay of active Neq DNA polymerase with 50 mM Mops-NaOH buffer, 50 mM Tris-HCl buffer and 50 mM Glycine-NaOH buffer, respectively. A closed circle (●), a closed triangle (▲) and a closed square (■) show the results of the 3'→5' exonuclease activity assay of Neq L with 50 mM Mops-NaOH buffer, 50 mM Tris-HCl buffer and 50 mM Glycine-NaOH buffer, respectively.

In order to investigate the effects of divalent cations on the proofreading activity of Neq L and active Neq DNA polymerase, the proofreading activity was measured at various concentrations of $MgCl_2$ in the absence of dNTPs. As a result, the active Neq DNA polymerase displayed maximal activity at 6 mM magnesium ions ($Mg^{2+}$), and Neq L displayed maximal activity at 3 mM magnesium ions ($Mg^{2+}$) (see, Panel C, FIG. 8). Panel C of FIG. 8 shows the effects of magnesium ions on the 3'→5' exonuclease activity of Neq L and active Neq DNA polymerase. In panel C of FIG. 8, an open circle (○) and a closed circle (●) show the results of the 3'→5' exonuclease activity assay of active Neq DNA and Neq L, respectively.

In order to investigate the effects of KCl on the proofreading activity of Neq L and active Neq DNA polymerase, the proofreading activity was measured at various concentrations of KCl in the absence of dNTPs. As a result, the active Neq DNA polymerase displayed maximal activity at 40 mM KCl, and Neq L displayed maximal activity at 0 mM KCl (see, Panel D, FIG. 8). Panel D of FIG. 8 shows the effects of KCl on the 3'→5' exonuclease activity of Neq L and active Neq DNA polymerase. In panel D of FIG. 8, an open circle (○) and a closed circle (●) show the results of the 3'→5' exonuclease activity assay of active Neq DNA and Neq L, respectively.

EXAMPLE 7

PCR using Active Neq DNA Polymerase

In order to perform PCR using the active Neq DNA polymerases purified in Example 3, four primer sets were first designed based on the genomic sequence of λ phage (see, Sanger, F. et al., 1982, *J. Mol. Biol.* 162, 729-773), as follows. A forward primer, lambda-1F (5'-AATAACGTCG-GCAACTTTGG-3' (SEQ ID NO:8), 20 bases), and a reverse primer, lambda-1R (3'-TCCTACTGACCACCGCATTG-5' (SEQ ID NO:9), 20 bases), were designed to amplify a 500-bp sequence upon PCR using the λ phage genomic DNA as a template. A forward primer, lambda-2F (5'-CAAAGGCG-GTTAAGGTGGTA-3' (SEQ ID NO:10), 20 bases), and a reverse primer, lambda-2R (3'-TGAGTAACAGGCCAT-GTCGG-5' (SEQ ID NO:11), 20 bases), were designed to amplify a 1-kb sequence upon PCR using the λ phage genomic DNA as a template. A forward primer, lambda-3F (5'-AGAAGTTCAGGAAGCGGTGA-3' (SEQ ID NO:12), 20 bases), and a reverse primer, lambda-3R (3'-AAGACG-CAGAGAAAAAGGCA-5' (SEQ ID NO:13), 20 bases), were designed to amplify a 2-kb sequence upon PCR using the λ phage genomic DNA as a template. A forward primer, lambda-4F (5'-CCGGTAATGGTGAGTTTGCT-3' (SEQ ID NO:14), 20 bases), and a reverse primer, lambda-4R (3'-TTACCGTTTCCGTGGTCATG-5' (SEQ ID NO:15), 20 bases), were designed to amplify a 4-kb sequence upon PCR using the λ phage genomic DNA as a template.

Then, PCR was performed using the λ phage genomic DNA as a template and the purified active Neq DNA polymerases, as follows. A PCR reaction mixture (50 µl) was prepared by mixing the purified active Neq DNA polymerase, 30 ng λ phage genomic DNA, 5 pmole lambda-2F primer and lambda-2R primer, 200 µM dNTP, and 1X reaction buffer (30 mM Tris-HCl (pH 8.0), 2 mM $MgCl_2$, 50 mM KCl, 0.01% BSA). After DNA denaturation at 95° C. for 10 min, the following three steps: DNA denaturation at 94° C. for 1 min, primer annealing at 58° C. for 1 min, and DNA extension at 72° C. for 2 min, were repeated 25 times, followed by a final DNA extension at 72° C. for 5 min. The PCR reaction mixture was then electrophoresed on an agarose gel along with a DNA size marker in order to determine whether PCR amplification occurred. As a result, the active Neq DNA polymerases having DNA polymerization activity, Neq C and Neq P, were found to be applicable to PCR.

In addition, PCR was carried out using Neq C and Neq P under various conditions as described below in order to investigate the optimal composition of reaction buffer for PCR using these enzymes and to confirm that the active Neq DNA polymerases, Neq C and Neq P, are the same enzymes displaying PCR results consistent with the results with respect to biochemical properties.

Figure 9:
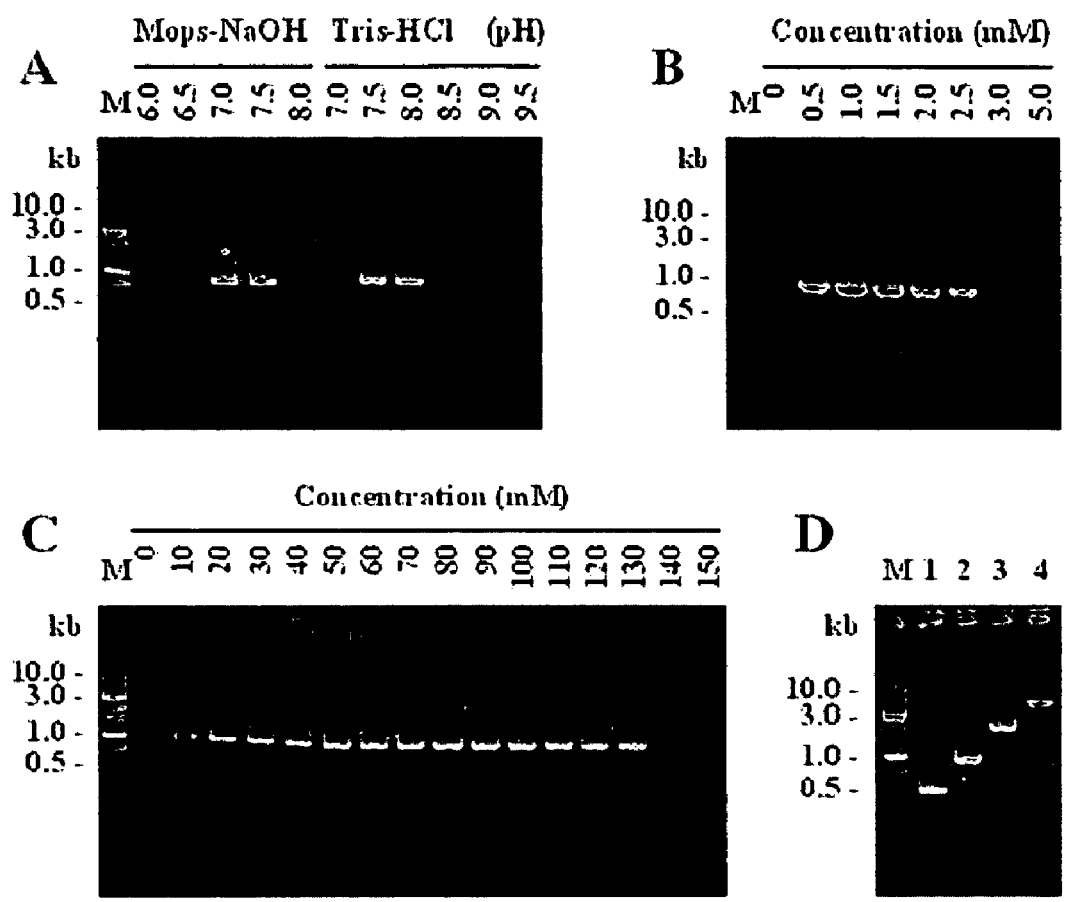
FIG. 9 shows the results of PCR using active Neq DNA polymerase.

In order to determine the optimal pH for PCR using the active Neq DNA polymerase, PCR was carried out using 50 mM buffer at a pH ranging from 6.0 to 9.5 (50 mM Mops-NaOH buffer of pH 6.0-8.0, 50 mM Tris-HCl buffer of pH 7.0-9.5) instead of 30 mM Tris-HCl (pH 8.0) buffer. The PCR amplification occurred in Mops-NaOH buffer at pH 7.0-7.5 and Tris-HCl buffer at pH 7.5-8.0, and the optimal pH was found to be pH 7.5 using Tris-HCl buffer (see, Panel A, FIG. 9). Panel A of FIG. 9 shows the results of PCR using active Neq DNA polymerase according to pH. In panel A of FIG. 9, lane M has a DNA size marker loaded thereon.

In order to determine the optimal $MgCl_2$ concentration for PCR using the active Neq DNA polymerase, PCR was carried out as described above at various concentrations of $MgCl_2$. The PCR amplification occurred at 0.5-3.0 mM $MgCl_2$, and the optimal $MgCl_2$ concentration was 1 mM (see, Panel B, FIG. 9). Panel B of FIG. 9 shows the results of PCR using active Neq DNA polymerase according to $MgCl_2$ concentration. In panel B of FIG. 9, lane M has a DNA size marker loaded thereon.

In order to determine the optimal KCl concentration for PCR using the active Neq DNA polymerase, PCR was carried out as described above at various concentrations of KCl. The PCR amplification occurred at 10-130 mM KCl, and the optimal KCl concentration was 90 mM (see, Panel C, FIG. 9). Panel C of FIG. 9 shows the results of PCR using active Neq DNA polymerase according to KCl concentration. In panel C of FIG. 9, lane M has a DNA size marker loaded thereon.

PCR was carried out in the thus-determined optimal reaction buffer (30 mM Tris-HCl (pH 7.5), 1 mM $MgCl_2$, 90 mM KCl, 0.01% BSA) using the λ phage genomic DNA as a template and the purified active Neq DNA polymerases in order to obtain amplification products having various sizes. A PCR reaction mixture (50 µl) was prepared by mixing the purified active Neq DNA polymerase, 30 ng λ phage genomic DNA, 5 pmole of a set of forward and reverse primers primer, 200 pM dNTP, and 1X optimal reaction buffer for active Neq DNA polymerase. After DNA denaturation at 95° C. for 10 min, the following three steps: DNA denaturation at 94° C. for 1 min, primer annealing at 56° C. for 1 min and DNA extension at 72° C. for 10 min, were repeated 25 times, followed by final DNA extension at 72° C. for 5 min. The PCR reaction mixture was then electrophoresed on an agarose gel along with a DNA size marker. As a result, PCR using the active Neq DNA polymerase was found to enable the amplification of a minimal 4 kb sequence in the optimal reaction buffer (see, Panel D, FIG. 9). Panel D of FIG. 9 shows the results of PCR using active Neq DNA polymerase in the optimal reaction buffer. In panel D of FIG. 9, each lane is as follows: lane M, DNA size marker; lane 1, amplification product (500 bp) of PCR using a set of lambda-1F and lambda-1R primers; lane 2, amplification product (1 kb) of PCR using a set of lambda-2F and lambda-2R primers; lane 3, amplification product (2 kb) of PCR using a set of lambda-3F and lambda-3R primers; lane 4, amplification product (4 kb) of PCR using a set of lambda-4F and lambda-4R primers.

The results of PCR with the active Neq DNA polymerase indicate that the active Neq DNA polymerases, Neq C and Neq P, are useful enzymes capable of being used in PCR, which a technique is applicable to various fields.

EXAMPLE 8

PCR using Active Neq DNA Polymerase in the Presence of dUTP

Figure 10:
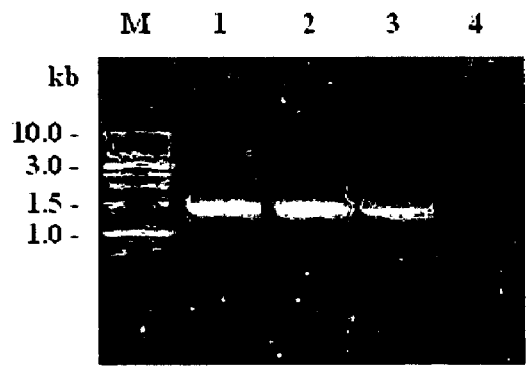
FIG. 10 shows a comparison of PCR results using active Neq DNA polymerase in the presence of dUTP with PCR results using Taq DNA polymerase and Pfu DNA polymerase in the presence of dUTP.

In order to perform PCR using the active Neq DNA polymerases purified in Example 3 in the presence of dUTP instead of dTTP, primers complementary to the 5'-end and 3'-end were first designed based on the nucleotide sequence of the *Thermus* sp. X-1 alkaline phosphatase gene. A 5'-end primer, TXAPF (5'-NNNNCATATGAAGCGAAGGGA-CATCCTG-3' (SEO ID NO:16), 28 bases), and a 3'-end primer, TXAPR (3'-GCTCCTGCAGACCCGGAT-TCAGCTGNNNN-5' (SEQ ID NO:17), 29 bases), were designed to amplify a 1.5-kb sequence upon PCR using the *Thermus* sp. X-1 genomic DNA as a template. Then, PCR was carried out using the *Thermus* sp. X-1 genomic DNA as a template, and the purified active Neq DNA polymerases, as follows. A PCR reaction mixture (50 µl) was prepared by mixing the purified active Neq DNA polymerase, 0.1 µg *Thermus* sp. X-1 genomic DNA, 5 pmole 5'-end primer and 3'-end primer, 200 µM dATP, 200 µM dCTP, 200 µM dGTP, 200 µM dUTP, and 1× optimal reaction buffer for active Neq DNA polymerase. After DNA denaturation at 95° C. for 10 min, the following three steps: DNA denaturation at 94° C. for 1 min, primer annealing at 56° C. for 1 min, and DNA extension at 72° C. for 2 min, were repeated 25 times, followed by final DNA extension at 72° C. for 5 min. The PCR reaction mixture was then electrophoresed on an agarose gel along with a DNA size marker. As a result, the active Neq DNA polymerases, Neq C and Neq P, were found to be applicable to PCR in the presence of dUTP (see, FIG. 10). FIG. 10 shows a comparison of PCR results using active Neq DNA polymerase in the presence of dUTP with PCR results using Taq DNA polymerase and Pfu DNA polymerase in the presence of dUTP. In FIG. 10, each lane is as follows: lane M, DNA size marker; lane 1, reaction mixture of PCR using the active Neq DNA polymerase Neq C in the presence of dUTP; lane 2, reaction mixture of PCR using the active Neq DNA polymerase Neq P in the presence of dUTP; lane 3, comparative reaction mixture of PCR using Tag DNA polymerase in the presence of dUTP; lane 4, comparative reaction mixture of PCR using Pfu DNA polymerase in the presence of dUTP.

The results of PCR with the active Neq DNA polymerase in the presence of dUTP indicate that the active Neq DNA polymerases, Neq C and Neq P, are excellent DNA polymerases very suitable for use in PCR for diagnosis and other purposes.

INDUSTRIAL APPLICABILITY

As described in detail and proven above, the present invention provides methods of preparing an active Neq DNA polymerase using a genetic engineering technique from the two genes coding for Neq DNA polymerase, the genes encoding polypeptides not having DNA polymerization activity alone. The active Neq DNA polymerase prepared by the methods, which has high proofreading activity and DNA polymerization activity, may be used in various nucleic acid polymerization reactions, such as general PCR and PCR in the presence of dUTP.

The invention claimed is:

1. A method of preparing an active Neq DNA polymerase, comprising:
   transforming a recombinant vector into a host cell, wherein the recombinant vector comprises the gene coding for the large fragment of Neq DNA polymerase and the gene coding for the small fragment of Neq DNA polymerase, and expresses the large and small fragments of Neq DNA polymerase;
   cultivating a resulting transformant;
   lysing said transformant to yield a cell lysate
   inducing in vitro protein trans-splicing of the large fragment of Neq DNA polymerase and the small fragment of Neq DNA polymerase in said cell lysate; and
   purifying the active Neq DNA polymerase.

2. The method according to claim 1, wherein the protein trans-splicing is induced by incubating cell lysates at 50° C. to 100° C.

3. A method of preparing an active Neq DNA polymerase, comprising:
   transforming a recombinant vector which comprises the extein-encoding region of the gene for the Neq DNA polymerse large fragment and the extein-encoding region of the gene for the Neq DNA polymerase small fragment, wherein the extein-encoding region of the gene for the Neq DNA polymerase large fragment is located upstream and the extein-encoding region of the gene for the Neq DNA polymerase small fragment is located downstream in a 5' to 3' direction, and expresses an active DNA polymerase being translated into a single polypeptide into a host cell;
   cultivating a resulting transformant; and
   purifying the active Neq DNA polymerase.

4. The method according to claim 1, wherein the recombinant vector separately expresses the Neq DNA polymerase large fragment and the Neq DNA polymerase small fragment from separate promoters.

5. The method according to claim 1, wherein the recombinant vector expresses the Neq DNA polymerase large fragment and the Neq DNA polymerase small fragment from a single promoter, and a ribosome binding site is located between the Neq DNA polymerase large fragment-encoding gene and the Neq DNA polymerase small fragment-encoding gene.

6. The method according to claim 5, wherein the recombinant vector is pENPC.

7. The method according to claim 3, wherein the recombinant vector is pENPP.

* * * * *

```
SEQUENCE LISTING

<160> NUMBER OF SEQ ID NOS: 22

<210> SEQ ID NO 1
<211> LENGTH: 31
<212> TYPE: DNA
<213> ORGANISM: Artificial Sequence
<220> FEATURE:
<223> OTHER INFORMATION: Synthetic

<400> SEQUENCE: 1
attatagcat atgttacacc aactccccac g                              31

<210> SEQ ID NO 2
<211> LENGTH: 37
<212> TYPE: DNA
<213> ORGANISM: Artificial Sequence
<220> FEATURE:
<223> OTHER INFORMATION: Synthetic

<400> SEQUENCE: 2
atctctcgag attattttta ttttcatatt ccttggc                        37

<210> SEQ ID NO 3
<211> LENGTH: 33
<212> TYPE: DNA
<213> ORGANISM: Artificial Sequence
<220> FEATURE:
<223> OTHER INFORMATION: Synthetic

<400> SEQUENCE: 3
taatttacat atgcgctatc ttggcaaaaa gag                            33

<210> SEQ ID NO 4
<211> LENGTH: 57
<212> TYPE: DNA
<213> ORGANISM: Artificial Sequence
<220> FEATURE:
<223> OTHER INFORMATION: Synthetic

<400> SEQUENCE: 4
cgggatccat taattatatc tccttcttat catttaaaga aatctgttag tttttg    57

<210> SEQ ID NO 5
<211> LENGTH: 40
<212> TYPE: DNA
<213> ORGANISM: Artificial Sequence
<220> FEATURE:
```

<223> OTHER INFORMATION: Synthetic

<400> SEQUENCE: 5
cgggatcctc attaattatt tttattttca tattccttgg          40

<210> SEQ ID NO 6
<211> LENGTH: 39
<212> TYPE: DNA
<213> ORGANISM: Artificial Sequence
<220> FEATURE:
<223> OTHER INFORMATION: Synthetic

<400> SEQUENCE: 6
taatgaatcg gtatctccat aaattacttt gaatccttc          39

<210> SEQ ID NO 7
<211> LENGTH: 37
<212> TYPE: DNA
<213> ORGANISM: Artificial Sequence
<220> FEATURE:
<223> OTHER INFORMATION: Synthetic

<400> SEQUENCE: 7
atttatggag ataccgattc attattcatt tctgggg          37

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
aataacgtcg gcaactttgg          20

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
gttacgccac cagtcatcct          20

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
caaaggcggt taaggtggta          20

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
ggctgtaccg gacaatgagt          20

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
agaagttcag gaagcggtga         20

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
acggaaaaag agacgcagaa         20

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
ccggtaatgg tgagtttgct         20

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
gtactggtgc ctttgccatt         20

<210> SEQ ID NO 16
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is a, c, g, or t

<400> SEQUENCE: 16
nnnncatatg aagcgaaggg acatcctg         28

<210> SEQ ID NO 17
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is a, c, g, or t

<400> SEQUENCE: 17
nnnngtcgac ttaggcccag acgtcctcg         29

<210> SEQ ID NO 18
<211> LENGTH: 801
<212> TYPE: PRT
<213> ORGANISM: Nanoarchaeum Equitans

<400> SEQUENCE: 18

```
Met Leu His Gln Leu Pro Thr Met Val Val Glu Glu Lys Ala Val Lys
1               5                   10                  15

Glu Glu Glu Gly Tyr Ser Val Leu Lys Cys Tyr Trp Ile Asn Ile Glu
            20                  25                  30

Asn Thr Pro Leu Asp Glu Val Ile Leu Ile Gly Lys Asp Glu Asn Asn
        35                  40                  45

Arg Ala Cys Glu Val Ile Ile Pro Tyr Lys Trp Tyr Phe Tyr Phe Glu
    50                  55                  60

Gly Asp Ile Lys Asp Leu Glu Glu Phe Ala Asn Asn Lys Lys Ile Lys
65                  70                  75                  80

Ile Glu Tyr Thr Lys Glu Gln Lys Lys Tyr Ile Glu Lys Pro Lys Asp
                85                  90                  95

Val Tyr Lys Val Tyr Val Leu His Lys His Tyr Pro Ile Leu Lys Glu
            100                 105                 110

Phe Ile Lys Glu Lys Gly Tyr Lys Lys Tyr Glu Thr Asp Ile Asn Val
        115                 120                 125

Tyr Arg Lys Phe Leu Ile Asp Lys Gly Ile Glu Pro Phe Glu Trp Phe
    130                 135                 140

Glu Val Glu Gly Lys Ile Leu Leu Ser Thr Ser Asn Lys Val Arg Ile
145                 150                 155                 160

Lys Ala Gln Ser Ile Lys Arg Leu Tyr Glu Lys Thr Lys Pro Ser Val
                165                 170                 175

Leu Ala Phe Asp Ile Glu Val Tyr Ser Glu Ala Phe Pro Asn Pro Glu
            180                 185                 190

Lys Asp Lys Ile Ile Ser Ile Ala Leu Tyr Gly Asp Asn Tyr Glu Gly
        195                 200                 205

Val Ile Ser Tyr Lys Gly Glu Pro Thr Ile Lys Val Asn Thr Glu Tyr
    210                 215                 220

Glu Leu Ile Glu Lys Phe Val Glu Ile Ile Glu Ser Leu Lys Pro Asp
225                 230                 235                 240

Ile Ile Val Thr Tyr Asn Gly Asp Asn Phe Asp Ile Asp Phe Leu Val
                245                 250                 255

Lys Arg Ala Ser Leu Tyr Asn Ile Arg Leu Pro Ile Lys Leu Val Asn
            260                 265                 270

Lys Lys Glu Pro Thr Tyr Asn Phe Arg Glu Ser Ala His Val Asp Leu
        275                 280                 285

Tyr Lys Thr Ile Thr Thr Ile Tyr Lys Thr Gln Leu Ser Thr Gln Thr
    290                 295                 300

Tyr Ser Leu Asn Glu Val Ala Lys Glu Ile Leu Gly Glu Glu Lys Ile
305                 310                 315                 320

Tyr Asp Tyr Glu Asn Met Leu Tyr Asp Trp Ala Ile Gly Asn Tyr Asn
                325                 330                 335

Lys Val Phe Glu Tyr Asn Leu Lys Asp Ala Glu Leu Thr Tyr Lys Leu
            340                 345                 350

Phe Lys Tyr Tyr Glu Asn Asp Leu Leu Glu Leu Ala Arg Leu Val Asn
        355                 360                 365

Gln Pro Leu Phe Asp Val Ser Arg Phe Ser Tyr Ser Asn Ile Val Glu
    370                 375                 380
```

-continued

```
Trp Tyr Leu Ile Lys Lys Ser Arg Lys Tyr Asn Glu Ile Val Pro Asn
385                 390                 395                 400

Lys Pro Lys Met Glu Glu Val Glu Arg Arg Lys Leu Asn Thr Tyr Ala
            405                 410                 415

Gly Ala Phe Val Tyr Glu Pro Lys Pro Gly Leu Tyr Glu Asn Leu Ala
            420                 425                 430

Val Leu Asp Phe Ala Ser Leu Tyr Pro Ser Ile Ile Leu Glu His Asn
        435                 440                 445

Val Ser Pro Gly Thr Ile Tyr Cys Glu His Asp Asp Cys Lys Gln Asn
    450                 455                 460

Gly Val Glu Ala Ile Ile Asn Asn Glu Lys Lys Tyr Val Trp Phe Cys
465                 470                 475                 480

Lys Lys Val Lys Gly Phe Ile Pro Thr Val Leu Glu His Leu Tyr Thr
                485                 490                 495

Lys Arg Leu Glu Leu Lys Arg Lys Leu Lys Glu Leu Asp Arg Asp Ser
            500                 505                 510

Glu Glu Tyr Lys Ile Ile Asn Ala Lys Gln Ala Val Leu Lys Ile Ile
            515                 520                 525

Ile Asn Ala Thr Tyr Gly Tyr Met Gly Phe Pro Asn Ala Arg Trp Tyr
        530                 535                 540

Cys Ile Asp Cys Ala Ala Ala Val Ala Ala Trp Gly Arg Lys Tyr Ile
545                 550                 555                 560

Asn Tyr Ile Leu Lys Arg Ala Glu Glu Glu Gly Phe Lys Val Ile Tyr
                565                 570                 575

Gly Asp Thr Asp Ser Leu Phe Ile Ser Gly Asp Lys Asp Val Lys Leu
            580                 585                 590

Glu Phe Leu Glu Lys Val Asn Lys Glu Leu Pro Gly Lys Ile Gln Leu
            595                 600                 605

Asp Leu Glu Asp Phe Tyr Val Arg Gly Ile Phe Val Lys Lys Arg Gly
        610                 615                 620

Glu Gln Lys Gly Ala Lys Lys Tyr Ala Leu Leu Ser Glu Gln Gly
625                 630                 635                 640

Tyr Ile Lys Leu Arg Gly Phe Glu Ala Val Arg Thr Asp Trp Ala Pro
                645                 650                 655

Ile Val Lys Glu Val Gln Thr Lys Leu Leu Glu Ile Leu Leu Lys Glu
            660                 665                 670

Gly Asn Ile Glu Lys Ala Arg Gln Tyr Ile Lys Glu Ile Ile Arg Lys
            675                 680                 685

Leu Arg Asn Arg Glu Ile Pro Trp Glu Lys Leu Leu Ile Thr Glu Thr
        690                 695                 700

Ile Arg Lys Pro Leu Glu Lys Tyr Lys Val Glu Ala Pro His Val Ala
705                 710                 715                 720

Ala Ala Lys Lys Tyr Lys Arg Leu Gly Tyr Lys Val Met Pro Gly Phe
                725                 730                 735

Arg Val Arg Tyr Leu Val Val Gly Ser Thr Gly Arg Val Ser Asp Arg
            740                 745                 750

Ile Lys Ile Asp Lys Glu Val Arg Gly Asn Glu Tyr Asp Pro Glu Tyr
        755                 760                 765

Tyr Ile Glu Lys Gln Leu Leu Pro Ala Val Glu Gln Ile Leu Glu Ser
    770                 775                 780

Val Gly Ile Lys Asp Thr Phe Thr Gly Lys Lys Leu Thr Asp Phe Phe
785                 790                 795                 800
```

Lys

<210> SEQ ID NO 19
<211> LENGTH: 809
<212> TYPE: PRT
<213> ORGANISM: Methanothermobacter thermautotrophicus str. Delta H

<400> SEQUENCE: 19

```
Met Glu Asp Tyr Arg Met Val Leu Leu Asp Ile Asp Tyr Val Thr Val
1               5                   10                  15

Asp Glu Val Pro Val Ile Arg Leu Phe Gly Lys Asp Lys Ser Gly Gly
            20                  25                  30

Asn Glu Pro Ile Ile Ala His Asp Arg Ser Phe Arg Pro Tyr Ile Tyr
        35                  40                  45

Ala Ile Pro Thr Asp Leu Asp Glu Cys Leu Arg Leu Glu Glu Leu
    50                  55                  60

Glu Leu Glu Lys Leu Glu Val Lys Glu Met Arg Asp Leu Gly Arg Pro
65                  70                  75                  80

Thr Glu Val Ile Arg Ile Glu Phe Arg His Pro Gln Asp Val Pro Lys
                85                  90                  95

Ile Arg Asp Arg Ile Arg Asp Leu Glu Ser Val Arg Asp Ile Arg Glu
            100                 105                 110

His Asp Ile Pro Phe Tyr Arg Arg Tyr Leu Ile Asp Lys Ser Ile Val
        115                 120                 125

Pro Met Glu Glu Leu Glu Phe Gln Gly Val Glu Val Asp Ser Ala Pro
    130                 135                 140

Ser Val Thr Thr Asp Val Arg Thr Val Glu Val Thr Gly Arg Val Gln
145                 150                 155                 160

Ser Thr Gly Ser Gly Ala His Gly Leu Asp Ile Leu Ser Phe Asp Ile
                165                 170                 175

Glu Val Arg Asn Pro His Gly Met Pro Asp Pro Glu Lys Asp Glu Ile
            180                 185                 190

Val Met Ile Gly Val Ala Gly Asn Met Gly Tyr Glu Ser Val Ile Ser
        195                 200                 205

Thr Ala Gly Asp His Leu Asp Phe Val Glu Val Val Glu Asp Glu Arg
    210                 215                 220

Glu Leu Leu Glu Arg Phe Ala Glu Ile Val Ile Asp Lys Lys Pro Asp
225                 230                 235                 240

Ile Leu Val Gly Tyr Asn Ser Asp Asn Phe Asp Phe Pro Tyr Ile Thr
                245                 250                 255

Arg Arg Ala Ala Ile Leu Gly Ala Glu Leu Asp Leu Gly Trp Asp Gly
            260                 265                 270

Ser Lys Ile Arg Thr Met Arg Arg Gly Phe Ala Asn Ala Thr Ala Ile
        275                 280                 285

Lys Gly Thr Val His Val Asp Leu Tyr Pro Val Met Arg Arg Tyr Met
    290                 295                 300

Asn Leu Asp Arg Tyr Thr Leu Glu Arg Val Tyr Gln Glu Leu Phe Gly
305                 310                 315                 320

Glu Glu Lys Ile Asp Leu Pro Gly Asp Arg Leu Trp Glu Tyr Trp Asp
                325                 330                 335

Arg Asp Glu Leu Arg Asp Glu Leu Phe Arg Tyr Ser Leu Asp Asp Val
            340                 345                 350

Val Ala Thr His Arg Ile Ala Glu Lys Ile Leu Pro Leu Asn Leu Glu
        355                 360                 365
```

-continued

```
Leu Thr Arg Leu Val Gly Gln Pro Leu Phe Asp Ile Ser Arg Met Ala
    370                 375                 380

Thr Gly Gln Gln Ala Glu Trp Phe Leu Val Arg Lys Ala Tyr Gln Tyr
385                 390                 395                 400

Gly Glu Leu Val Pro Asn Lys Pro Ser Gln Ser Asp Phe Ser Ser Arg
                405                 410                 415

Arg Gly Arg Arg Ala Val Gly Gly Tyr Val Lys Glu Pro Glu Lys Gly
            420                 425                 430

Leu His Glu Asn Ile Val Gln Phe Asp Phe Arg Ser Leu Tyr Pro Ser
                435                 440                 445

Ile Ile Ile Ser Lys Asn Ile Ser Pro Asp Thr Leu Thr Asp Asp Glu
    450                 455                 460

Glu Ser Glu Cys Tyr Val Ala Pro Glu Val Gly Tyr Arg Phe Arg Lys
465                 470                 475                 480

Ser Pro Arg Gly Phe Val Pro Ser Val Ile Gly Glu Ile Leu Ser Glu
                485                 490                 495

Arg Val Arg Ile Lys Glu Glu Met Lys Gly Ser Asp Asp Pro Met Glu
            500                 505                 510

Arg Lys Ile Leu Asn Val Gln Gln Glu Ala Leu Lys Arg Leu Ala Asn
        515                 520                 525

Thr Met Tyr Gly Val Tyr Gly Tyr Ser Arg Phe Arg Trp Tyr Ser Met
    530                 535                 540

Glu Cys Ala Glu Ala Ile Thr Ala Trp Gly Arg Asp Tyr Ile Lys Lys
545                 550                 555                 560

Thr Ile Lys Thr Ala Glu Glu Phe Gly Phe His Thr Val Tyr Ala Asp
                565                 570                 575

Thr Asp Gly Phe Tyr Ala Thr Tyr Arg Gly Met Ser Gln Leu Ser Lys
            580                 585                 590

Val Glu Asp Glu Ile Leu Ser Gln Val Lys Arg Phe Leu Lys His Ile
        595                 600                 605

Asn Ser Asn Leu Pro Glu Gly Met Glu Leu Glu Phe Glu Gly Phe Tyr
    610                 615                 620

Arg Arg Gly Phe Phe Val Thr Lys Lys Arg Tyr Ala Leu Ile Glu Asp
625                 630                 635                 640

Asp Thr Ile Val Ala Lys Gly Leu Glu Leu Val Arg Arg Asp Trp Ala
                645                 650                 655

Pro Ile Ala Lys Lys Thr Gln Arg Lys Val Leu Met Ala Ile Leu Arg
            660                 665                 670

Asp Gly Ser Pro Glu Lys Ala Arg Glu Ile Ile Arg Glu Val Val Gly
        675                 680                 685

Arg Ile Arg Arg Gly Asp Val Glu Leu Asp Asp Leu Val Ile His Thr
    690                 695                 700

Gln Ile Thr Arg Asp Leu Ser Glu Tyr Lys Gln Ile Gly Pro His Val
705                 710                 715                 720

Ile Ala Ala Lys Arg Ser Leu Glu Lys Gly Arg Arg Val Glu Arg Gly
                725                 730                 735

Ser Ile Val Arg Tyr Ile Ile Val Lys Gly Arg Gly Pro Ile Ser Gln
            740                 745                 750

Arg Ala Phe Pro Val Glu Asp Ala Glu Gly Met Gly Tyr Asp Pro Asp
        755                 760                 765

Tyr Tyr Ile Glu Asn Gln Val Met Ala Ala Val Ser Arg Ile Met Ser
    770                 775                 780

Ser Leu Gly Tyr Ser Thr Glu Asp Met Asn Ser Leu Ser Ser Gly Glu
```

```
                785                 790                 795                 800
Arg Gln Ser Ser Leu Asp Ala Phe Phe
                805

<210> SEQ ID NO 20
<211> LENGTH: 775
<212> TYPE: PRT
<213> ORGANISM: Pyrococcus furiosus DSM 3638

<400> SEQUENCE: 20

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350
```

```
Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
        370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
                420                 425                 430

Asp Ile Ala Pro Gln Val Gly His Lys Phe Cys Lys Asp Ile Pro Gly
            435                 440                 445

Phe Ile Pro Ser Leu Leu Gly His Leu Leu Glu Glu Arg Gln Lys Ile
450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
                500                 505                 510

Ser Val Thr Ala Trp Gly Arg Lys Tyr Ile Glu Leu Val Trp Lys Glu
            515                 520                 525

Leu Glu Glu Lys Phe Gly Phe Lys Val Leu Tyr Ile Asp Thr Asp Gly
        530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
                580                 585                 590

Lys Arg Tyr Ala Val Ile Asp Glu Glu Gly Lys Val Ile Thr Arg Gly
            595                 600                 605

Leu Glu Ile Val Arg Arg Asp Trp Ser Glu Ile Ala Lys Glu Thr Gln
        610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
                660                 665                 670

Glu Tyr Lys Ala Ile Gly Pro His Val Ala Val Ala Lys Lys Leu Ala
            675                 680                 685

Ala Lys Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
                740                 745                 750

Lys Glu Asp Leu Arg Tyr Gln Lys Thr Arg Gln Val Gly Leu Thr Ser
            755                 760                 765

Trp Leu Asn Ile Lys Lys Ser
```

```
                 770                 775

<210> SEQ ID NO 21
<211> LENGTH: 130
<212> TYPE: PRT
<213> ORGANISM: Nanoarchaeum Equitans

<400> SEQUENCE: 21

Ser Ile Met Asp Thr Glu Ile Glu Val Ile Glu Asn Gly Ile Lys Lys
1               5                   10                  15

Lys Glu Lys Leu Ser Asp Leu Phe Asn Lys Tyr Tyr Ala Gly Phe Gln
            20                  25                  30

Ile Gly Glu Lys His Tyr Ala Phe Pro Pro Asp Leu Tyr Val Tyr Asp
        35                  40                  45

Gly Glu Arg Trp Val Lys Val Tyr Ser Ile Ile Lys His Glu Thr Glu
    50                  55                  60

Thr Asp Leu Tyr Glu Ile Asn Gly Ile Thr Leu Ser Ala Asn His Leu
65                  70                  75                  80

Val Leu Ser Lys Gly Asn Ile Trp Val Lys Ala Lys Glu Tyr Glu Asn
                85                  90                  95

Lys Asn Asn Met Arg Tyr Leu Gly Lys Lys Arg Val Ile Leu Tyr Asp
            100                 105                 110

Leu Ser Thr Glu Ser Gly Lys Phe Tyr Val Asn Gly Leu Val Leu His
        115                 120                 125

Asn Thr
    130

<210> SEQ ID NO 22
<211> LENGTH: 160
<212> TYPE: PRT
<213> ORGANISM: Artificial Sequence
<220> FEATURE:
<223> OTHER INFORMATION: Synthetic

<400> SEQUENCE: 22

Cys Leu Ser Phe Gly Thr Glu Ile Leu Thr Val Glu Tyr Gly Pro Leu
1               5                   10                  15

Pro Ile Gly Lys Ile Val Ser Glu Glu Ile Asn Cys Ser Val Tyr Ser
            20                  25                  30

Val Asp Pro Glu Gly Arg Val Tyr Thr Gln Ala Ile Ala Gln Trp His
        35                  40                  45

Asp Arg Gly Glu Gln Glu Val Leu Glu Tyr Glu Leu Glu Asp Gly Ser
    50                  55                  60

Val Ile Arg Ala Thr Ser Asp His Arg Phe Leu Thr Thr Asp Tyr Gln
65                  70                  75                  80

Leu Leu Ala Ile Glu Glu Ile Phe Ala Arg Gln Leu Asp Leu Leu Thr
                85                  90                  95

Leu Glu Asn Ile Lys Gln Thr Glu Glu Ala Leu Asp Asn His Arg Leu
            100                 105                 110

Pro Phe Pro Leu Leu Asp Ala Gly Thr Ile Lys Met Val Lys Val Ile
        115                 120                 125

Gly Arg Arg Ser Leu Gly Val Gln Arg Ile Phe Asp Ile Gly Leu Pro
    130                 135                 140

Gln Asp His Asn Phe Leu Leu Ala Asn Gly Ala Ile Ala Ala Asn Cys
145                 150                 155                 160
```